United States Patent
Flamme et al.

(10) Patent No.: US 9,315,543 B2
(45) Date of Patent: *Apr. 19, 2016

(54) TYROSINE BASED LINKERS FOR THE RELEASABLE CONNECTION OF PEPTIDES

(71) Applicants: Bayer Intellectual Property GmbH, Monheim (DE); Bayer Pharma Aktiengesellschaft, Berlin (DE)

(72) Inventors: Ingo Flamme, Reichshof (DE); Johannes Köbberling, Neuss (DE); Hans-Georg Lerchen, Leverkusen (DE); Nils Griebenow, Dormagen (DE); Rudolf Schohe-Loop, Wuppertal (DE); Sven Wittrock, Wuppertal (DE); Ursula Krenz, Leichlingen (DE)

(73) Assignees: Bayer Intellectual Property GmbH, Monheim (DE); Bayer Pharma Aktiengesellschaft, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/355,836

(22) PCT Filed: Oct. 29, 2012

(86) PCT No.: PCT/EP2012/071373
§ 371 (c)(1),
(2) Date: May 1, 2014

(87) PCT Pub. No.: WO2013/064455
PCT Pub. Date: May 10, 2013

(65) Prior Publication Data
US 2015/0051160 A1 Feb. 19, 2015

(30) Foreign Application Priority Data

Nov. 3, 2011 (EP) .................................. 11187737

(51) Int. Cl.
*A61K 38/22* (2006.01)
*C07K 5/09* (2006.01)
*A61K 47/48* (2006.01)
*C07K 5/068* (2006.01)
*A61K 38/05* (2006.01)
*A61K 38/06* (2006.01)
*C07K 5/02* (2006.01)

(52) U.S. Cl.
CPC ............ *C07K 5/0815* (2013.01); *A61K 38/05* (2013.01); *A61K 38/06* (2013.01); *A61K 47/48* (2013.01); *C07K 5/06086* (2013.01); *C07K 5/0215* (2013.01)

(58) Field of Classification Search
None
See application file for complete search history.

(56) References Cited

U.S. PATENT DOCUMENTS

2009/0186832 A1 7/2009 Franklin et al.
2010/0111865 A1* 5/2010 Tolleshaug et al. ............ 424/9.1

FOREIGN PATENT DOCUMENTS

| EP | 0 296 811 | 6/1988 |
| WO | 02083180 A1 | 10/2002 |
| WO | 02089789 A1 | 11/2002 |
| WO | 2004043493 A1 | 5/2004 |
| WO | 2004019993 A1 | 11/2004 |
| WO | 2005099768 A2 | 10/2005 |
| WO | 2006136586 A2 | 12/2006 |

OTHER PUBLICATIONS

Johnson, Elizabeth R. and Matthay, Michael A; "Acute lung injury: epidemiology, pathogenesis, and treatment." J. Aerosol Med. Pulmon. Drug. Delv. (2010) 23(4) p243-252.*
Sainlos, Mattthiew and Imperiali, Barbara; "Tools for investigating peptide-protein interactions: peptide incorporation of environment-sensitive fluorophores through spps-based 'building block' approach." Nat. Protocol (2007) 2(12) p. 3210-3218.*
Ottinger, Elizabeth A. et al, "Synthesis of phosphotyrosine-containing peptides and their use as substrates for protein tyrosine phosphatases." Biochemistry (1993) 32(16) p. 4354-4361.*
Alberico et al., "Palladium-catalyzed sequential alkylation—alkenylation reactions: application towards the synthesis of polyfunctionalized fused aromatic rings," Tetrahedron, 2005, vol. 61, pp. 6283-6297.
Caliceti et al., "Pharmacokinetic and biodistribution properties of poly(ethylene glycol)—protein conjugates," Adv. Drug Del. Rev., 2003, vol. 55, pp. 1261-1277.
Na et al., "Monitoring of peptide acylation inside degrading PLGA microspheres by capillary electrophoresis and MALDI-TOF mass spectrometry," Journal of Controlled Release, 2003, vol. 92, pp. 291-299.
Greenwald et al., "Drug Delivery Systems Employing 1,4- or 1,6-Elimination: Poly(ethylene glycol) Prodrugs of Amine-Containing Compounds," Journal of Med. Chem., 1999, vol. 42, pp. 3657-3667.
Greenwald et al., "A New Aliphatic Amino Prodrug System for the Delivery of Small Molecules and Proteins Utilizing Novel PEG Derivatives," Journal of Med. Chem., 2004, vol. 47, pp. 726-734.
Peleg-Shulman et al., "Reversible PEGylation: A Novel Technology to Release Native Interferon α2 over a Prolonged Time Period," Journal of Med. Chem., 2004, vol. 47, pp. 4897-4904.
Rautio et al., "Prodrugs: design and clinical applications," Nature Reviews Drug Discovery, Mar. 2008, vol. 7, pp. 255-270.
Saari et al., "Cyclization-Activated Prodrugs. Basic Carbamates of 4-Hydroxyanisole," Journal of Med. Chem., 1990, vol. 33, No. 1, pp. 97-101.
Wermuth et al., Pure & Appl. Chem., 1998, vol. 70, No. 5, pp. 1129-1143.

* cited by examiner

*Primary Examiner* — Maury Audet
*Assistant Examiner* — Fred Reynolds
(74) *Attorney, Agent, or Firm* — Aseem V. Mehta

(57) ABSTRACT

The invention relates to novel tyrosine based linkers that allow the releasable connection of peptides or proteins with other molecular entities, e.g. polyethylene glycol, to processes for their preparation and their use for preparing medicaments for the treatment and/or prophylaxis of diseases.

6 Claims, No Drawings

TYROSINE BASED LINKERS FOR THE RELEASABLE CONNECTION OF PEPTIDES

The invention relates to novel tyrosine based linkers that allow the releasable connection of peptides or proteins with other molecular entities, e.g. polyethylene glycol, to processes for their preparation and their use for preparing medicaments for the treatment and/or prophylaxis of diseases.

Many therapeutically active peptides or proteins suffer from high clearance in vivo. Several approaches to form an injectable depot of such drugs exist that involve the use of macromolecules.

Polymer matrices that contain a drug molecule in a non covalently bound state are well known. These can also be injectable as hydro gels, micro particles or micelles. The release kinetics of such drug products can be quite unreliable with high inter patient variability. Production of such polymers can harm the sensitive drug substance or it can undergo side reactions with the polymer during its degradation (D. H. Lee et al., J. Contr. Rel., 2003, 92, 291-299).

Permanent PEGylation of peptides or proteins to enhance their solubility, reduce immunogenicity and increase half life by reducing renal clearance is a well known concept since early 1980s (Caliceti P., Veronese F. M., Adv. Drug Deliv. Rev. 2003, 55, 1261-1277). For several drugs this has been used with success, but with many examples the PEGylation reduces efficacy of drug substance to an extent that this concept is not suitable any more (T. Peleg-Shulman et al., J. Med. Chem., 2004, 47, 4897-4904).

A suitable alternative are polymer based prodrugs. The current definitions for prodrugs by the IUPAC state the following terms (International Union of Pure and Applied Chemistry and International Union of Biochemistry: GLOSSARY OF TERMS USED IN MEDICINAL CHEMISTRY (Recommendations 1998); in Pure & Appl. Chem. Vol 70, No. 5, 1998, p. 1129-1143):

Prodrug: A prodrug is any compound that undergoes biotransformation before exhibiting its pharmacological effects. Prodrugs can thus be viewed as drugs containing specialized non-toxic protective groups used in a transient manner to alter or to eliminate undesirable properties in the parent molecule.

Carrier-linked prodrug (Carrier prodrug): A carrier-linked prodrug is a prodrug that contains a temporary linkage of a given active substance with a transient carrier group that produces improved physicochemical or pharmacokinetic properties and that can be easily removed in vivo, usually by a hydrolytic cleavage.

Cascade prodrug: A cascade prodrug is a prodrug for which the cleavage of the carrier group becomes effective only after unmasking an activating group.

Several examples of PEG-based carrier prodrugs exist, most of them with the need for enzymatic activation of the linker between the active drug and the carrier, mostly initiated by enzymatic hydrolysis. Since esters are cleaved very readily and unpredictably in vivo, direct ester linkers for carrier pro drug have limitations to their usability (J. Rautio et al., Nature Reviews Drug discovery, 2008, 7 255-270).

Commonly used alternative approaches are cascading linkers attached to an amine functionality in the peptide or protein. In cascading linkers a masking group has to be removed as the rate limiting step in the cascade. This activates the linker to decompose in a second position to release the peptide or protein. Commonly the masking group can be removed by an enzymatic mechanism (R. B. Greenwald et al. in WO2002/089789, Greenwald, et al., J. Med. Chem. 1999, 42, 3657-3667, F. M. H. DeGroot et al. in WO2002/083180 and WO2004/043493, and D. Shabat et al. in WO2004/019993).

An alternative not relying on enzymatic activation is the concept of U. Hersel et al. in WO2005/099768. In their approach the masking group on a phenol is removed in a purely pH dependent manner by the attack of an internal nucleophile. This activates the linker for further decomposition.

As mentioned by U. Hersel et al. in WO2005/099768, "The disadvantage in the abovementioned prodrug systems described by Greenwald, DeGroot and Shabat is the release of potentially toxic aromatic small molecule side products like quinone methides after cleavage of the temporary linkage. The potentially toxic entities are released in a 1:1 stoichiometry with the drug and can assume high in vivo concentrations." The same problem holds true for the system by Hersel et al. as well.

For small organic molecules a plethora of different prodrug approaches exist (J. Rautio et al., Nature Reviews Drug discovery, 2008, 7 255-270). The approach used by U. Hersel et al. as release mechanism for their masking group has been used as a prodrug approach for phenolic groups of small molecules since the late 1980s. (W. S. Saari in EP 0296 811 and W. S. Saari et al., J. Med. Chem. 1990, Vol 33, No 1, p 97-101).

Alternative amine based prodrug system are based on the slow hydrolysis of bis-hydroxyethyl glycine as a cascading prodrug. The hydroxy groups of the bis-hydroxyethyl glycine are masked by esters that are prone to hydrolysis by esterases (R. Greenwald et al., J. Med. Chem. 2004, 47, 726-734 and D. Vetter et al. in WO 2006/136586).

In contrast to the prodrug approaches listed above, which are all based on masking amine functionalities, the current invention is based on masking the phenolic group of a tyrosine in peptides or proteins. A carrier-linked prodrug is used, based on the internal nucleophile assisted cleavage of a carbamate on this phenolic group. The key advantage to other prodrug classes mentioned above is the toxicological harmlessness of the linker decomposition product, a cyclic urea permanently attached to the carrier. Furthermore, the decomposition of the prodrug is not dependent on enzymatic mechanisms that might cause a high inter patient variability of cleavage kinetics. The cleavage mechanism is solely pH dependent as an internal amine that is protonated at acidic pH gets activated at higher (neutral) pH to act as a nucleophile attacking the phenolic carbamate based on the tyrosine.

In the context of the present invention, compounds are now described which encompass tyrosine amino acid based molecular entities that enable the construction of said carrier linker prodrugs of any peptide or protein that contains at least one tyrosine.

The present invention provides compounds of the formula

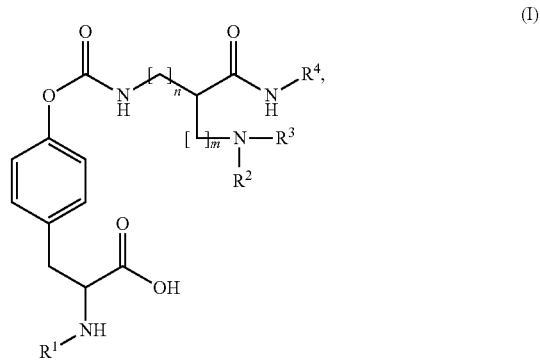

(I)

in which
n represents the number 0, 1, 2, 3 or 4,
m represents the number 0, 1, 2, 3 or 4,
where m and n together are the number 1, 2, 3, 4, 5 or 6,
$R^1$ represents tert-butyloxycarbonyl or (9H-fluoren-9-yl-methoxy)carbonyl,
$R^2$ represents tert-butyloxycarbonyl,
$R^3$ represents hydrogen, methyl, ethyl, n-propyl, isopropyl or benzyl,
$R^4$ represents a group of the formula

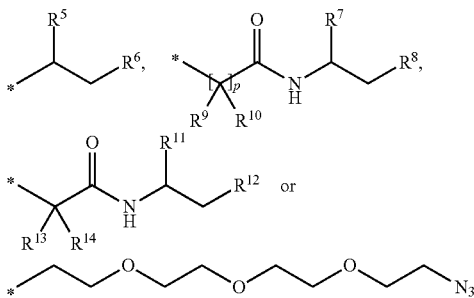

where
* is the point of attachment to the nitrogen,
p represents the number 1, 2, 3, 4 or 5,
$R^5$ represents hydrogen, aminocarbonyl, $(C_1-C_4)$-alkylaminocarbonyl, phenylaminocarbonyl or a group of the formula

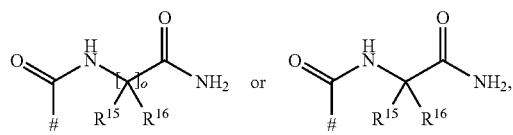

where
# is the point of attachment to the carbon atom,
o represents the number 1, 2, 3, 4 or 5,
$R^{15}$ represents hydrogen or $(C_1-C_4)$-alkyl,
$R^{16}$ represents hydrogen or $(C_1-C_4)$-alkyl,
$R^{17}$ represents the side group of a natural α-amino acid or its homologues or isomers,
and
$R^{18}$ represents hydrogen or methyl,
$R^6$ represents —S-trityl, thiolyl, azidyl, acetylenyl, hydroxycarbonyl or amine,
$R^7$ represents hydrogen or aminocarbonyl,
$R^8$ represents —S-trityl, thiolyl, azidyl, acetylenyl, hydroxycarbonyl or amine,
$R^9$ represents hydrogen or $(C_1-C_4)$-alkyl,
$R^{10}$ represents hydrogen or $(C_1-C_4)$-alkyl,
$R^{11}$ represents hydrogen or aminocarbonyl,
$R^{12}$ represents —S-trityl, thiolyl, azidyl, acetylenyl, hydroxycarbonyl or amine,
$R^{13}$ represents the side group of a natural α-amino acid or its homologues or isomers,
and
$R^{14}$ represents hydrogen or methyl,
and salts thereof, solvates thereof and the solvates of salts thereof.

Compounds according to the invention are the compounds of the formula (I) and the salts thereof, solvates thereof and solvates of the salts thereof, the compounds which are embraced by formula (I) and are of the formulae specified below and the salts thereof, solvates thereof and solvates of the salts thereof, and the compounds which are embraced by formula (I) and are specified below as working examples and salts thereof, solvates thereof and solvates of the salts thereof, if the compounds which are embraced by formula (I) and are specified below are not already salts, solvates and solvates of the salts.

Depending on their structure, the compounds according to the invention may exist in stereoisomeric forms (enantiomers, diastereomers). The invention therefore embraces the enantiomers or diastereomers and the particular mixtures thereof. The stereoisomerically homogeneous constituents can be isolated in a known manner from such mixtures of enantiomers and/or diastereomers.

When the compounds according to the invention can occur in tautomeric forms, the present invention embraces all tautomeric forms.

In the context of the present invention, preferred salts are physiologically acceptable salts of the compounds according to the invention. Also included are salts which are not suitable themselves for pharmaceutical applications, but, for example, can be used for the isolation or purification of the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluene-sulfonic acid, benzenesulfonic acid, naphthalenedisulfonic acid, acetic acid, trifluoroacetic acid, propionic acid, lactic acid, tartaric acid, maleic acid, citric acid, fumaric acid, maleic acid and benzoic acid.

Physiologically acceptable salts of the compounds according to the invention also include salts of customary bases, for example and with preference alkali metal salts (e.g. sodium and potassium salts), alkaline earth metal salts (e.g. calcium and magnesium salts) and ammonium salts derived from ammonia or organic amines having 1 to 16 carbon atoms, for example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the compounds according to the invention which, in the solid or liquid state, form a complex by coordination with solvent molecules. Hydrates are a specific form of the solvates, in which the coordination is with water. Preferred solvates in the context of the present invention are hydrates.

In the context of the present invention, the substituents have the following meaning unless otherwise specified:

$(C_1-C_4)$-Alkyl are in the context of the invention a straight-chain or branched alkyl radical having respectively 1 to 4 carbon atoms. Examples which may be preferably mentioned are: methyl, ethyl, n-propyl, isopropyl, n-butyl, iso-butyl, sec-butyl, tert-butyl.

$(C_1-C_4)$-Alkylaminocarbonyl in the context of the invention represents an aminocarbonyl group with a straight-chain or branched alkyl substituent which contains 1 to 4 carbon atoms. Examples which may be preferably mentioned are: methylaminocarbonyl, ethylaminocarbonyl, n-propylaminocarbonyl, isopropylaminocarbonyl, n-butylaminocarbonyl, iso-butylaminocarbonyl, sec-butylaminocarbonyl, tert-butylaminocarbonyl.

The side group of an α-amino acid in the meaning of $R^{13}$ and $R^{17}$ encompasses both the side groups of naturally occurring α-amino acids and the side groups of homologs and isomers of these α-amino acids. The α-amino acid may in this connection have both the L and the D configuration or else be a mixture of the L form and D form. Examples of side groups which may be mentioned are: hydrogen (glycine), methyl (alanine), propan-2-yl (valine), propan-1-yl (norvaline), 2-methylpropan-1-yl (leucine), 1-methylpropan-1-yl (isoleucine), butan-1-yl (norleucine), phenyl (2-phenylglycine), benzyl (phenylalanine), p-hydroxybenzyl (tyrosine), indol-3-ylmethyl (tryptophan), imidazol-4-ylmethyl (histidine), hydroxymethyl (serine), 2-hydroxyethyl (homoserine), 1-hydroxyethyl (threonine), mercaptomethyl (cysteine), methylthiomethyl (S-methylcysteine), 2-mercaptoethyl (homocysteine), 2-methylthioethyl (methionine), carbamoylmethyl (asparagine), 2-carbamoylethyl (glutamine), carboxymethyl (aspartic acid), 2-carboxyethyl (glutamic acid), 4-aminobutan-1-yl (lysine), 4-amino-3-hydroxybutan-1-yl (hydroxylysine), 3-aminopropan-1-yl (ornithine), 3-guanidinopropan-1-yl (arginine), 3-ureidopropan-1-yl (citrulline). Preferred α-amino acid side groups in the meaning of $R^2$ are hydrogen (glycine), methyl (alanine), propan-2-yl (valine), propan-1-yl (norvaline), imidazol-4-ylmethyl (histidine), hydroxymethyl (serine), 1-hydroxyethyl (threonine), carbamoylmethyl (asparagine), 2-carbamoylethyl (glutamine), 4-aminobutan-1-yl (lysine), 3-aminopropan-1-yl (ornithine), 3-guanidinopropan-1-yl (arginine). The L configuration is preferred in each case.

In the context of the invention modifier means other molecular entities, e.g. polyethylene glycol.

In the formulae of the group which may represent $R^4$, the end point of the line which is marked by an * is not a carbon atom or a $CH_2$ group, but is part of the bond to the atom to which $R^4$ is attached.

In the formulae of the group which may represent $R^5$, the end point of the line which is marked by an # is not a carbon atom or a $CH_2$ group, but is part of the bond to the atom to which $R^5$ is attached.

Preference is given to compounds of the formula (I) in which
n represents the number 0, 1, 2 or 3,
m represents the number 0, 1, 2 or 3,
where m and n together are the number 1, 2, 3 or 4,
$R^1$ represents tert-butyloxycarbonyl or (9H-fluoren-9-yl-methoxy)carbonyl,
$R^2$ represents tert-butyloxycarbonyl,
$R^3$ represents hydrogen, methyl, ethyl, n-propyl, isopropyl or benzyl,
$R^4$ represents a group of the formula

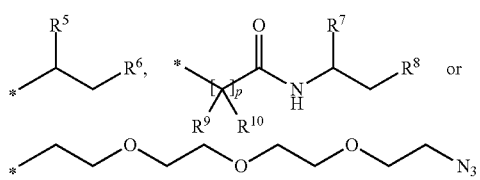

where
* is the point of attachment to the nitrogen,
p represents the number 1, 2, 3, 4 or 5,
$R^5$ represents hydrogen, aminocarbonyl or —(C=O)NHCH$_2$(C=O)NH$_2$,
$R^6$ represents —S-trityl,
$R^7$ represents hydrogen or aminocarbonyl,
$R^8$ represents —S-trityl,
$R^9$ represents hydrogen,
and
$R^{10}$ represents hydrogen.

Preference is also given to compounds of the formula (I) in which
n represents the number 2 or 3,
and
m represents the number 0,
or
n represents the number 0,
and
m represents the number 2 or 3,
$R^1$ represents tert-butyloxycarbonyl or (9H-fluoren-9-yl-methoxy)carbonyl,
$R^2$ represents tert-butyloxycarbonyl,
$R^3$ represents hydrogen, methyl, ethyl, n-propyl, isopropyl or benzyl,
$R^4$ represents a group of the formula

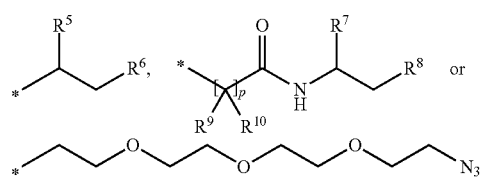

where
* is the point of attachment to the nitrogen,
p represents the number 1, 2, 3, 4 or 5,
$R^5$ represents hydrogen, aminocarbonyl or —(C=O)NHCH$_2$(C=O)NH$_2$,
$R^6$ represents —S-trityl,
$R^7$ represents hydrogen or aminocarbonyl,
$R^8$ represents —S-trityl,
$R^9$ represents hydrogen,
and
$R^{10}$ represents hydrogen.

Preference is also given to compounds of the formula (I) in which
n represents the number 2 or 3,
m represents the number 0,
$R^1$ represents tert-butyloxycarbonyl or (9H-fluoren-9-yl-methoxy)carbonyl,
$R^2$ represents tert-butyloxycarbonyl,
$R^3$ represents hydrogen or methyl,
$R^4$ represents a group of the formula

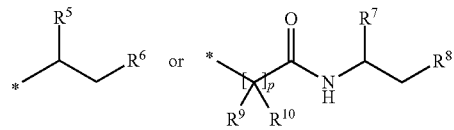

where
* is the point of attachment to the nitrogen,
p represents the number 1 or 5,
$R^5$ represents hydrogen, aminocarbonyl or —(C=O)NHCH$_2$(C=O)NH$_2$,
$R^6$ represents —S-trityl,
$R^7$ represents hydrogen or aminocarbonyl,
$R^8$ represents —S-trityl,
$R^9$ represents hydrogen, and $R^{10}$ represents hydrogen.

Preference is also given to compounds of the formula (I) in which n represents the number 0,
m represents the number 2 or 3,
$R^1$ represents tert-butyloxycarbonyl or (9H-fluoren-9-yl-methoxy)carbonyl,
$R^2$ represents tert-butyloxycarbonyl,
$R^3$ represents hydrogen or methyl,
$R^4$ represents a group of the formula

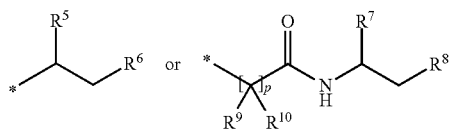

where
* is the point of attachment to the nitrogen,
p represents the number 1 or 5,
$R^5$ represents hydrogen, aminocarbonyl or —(C=O)NHCH$_2$(C=O)NH$_2$,
$R^6$ represents —S-trityl,
$R^7$ represents hydrogen or aminocarbonyl,
$R^8$ represents —S-trityl,
$R^9$ represents hydrogen,
and
$R^{10}$ represents hydrogen.

Preference is also given to compounds of the formula (I) in which n represents the number 2 or 3,
m represents the number 0,
$R^1$ represents tert-butyloxycarbonyl or (9H-fluoren-9-yl-methoxy)carbonyl,
$R^2$ represents tert-butyloxycarbonyl,
$R^3$ represents hydrogen or methyl,
$R^4$ represents a group of the formula

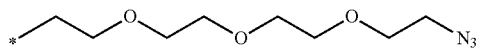

where
* is the point of attachment to the nitrogen.

Preference is also given to compounds of the formula (I) in which n represents the number 0, 1, 2 or 3,
m represents the number 0, 1, 2 or 3,
where m and n together are the number 1, 2, 3 or 4,
$R^1$ represents tert-butyloxycarbonyl or (9H-fluoren-9-yl-methoxy)carbonyl,
$R^2$ represents tert-butyloxycarbonyl,
$R^3$ represents hydrogen, methyl, ethyl, n-propyl, isopropyl or benzyl,
$R^4$ represents a group of the formula

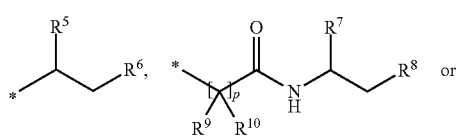

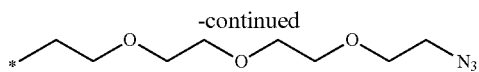

where
* is the point of attachment to the nitrogen,
p represents the number 1, 2, 3, 4 or 5,
$R^5$ represents hydrogen, aminocarbonyl, phenylaminocarbonyl or —(C=O)NHCH$_2$(C=O)NH$_2$,
$R^6$ represents —S-trityl,
$R^7$ represents hydrogen or aminocarbonyl,
$R^8$ represents —S-trityl,
$R^9$ represents hydrogen,
and
$R^{10}$ represents hydrogen.

Preference is also given to compounds of the formula (I) in which n represents the number 2 or 3,
and
m represents the number 0,
or
n represents the number 0,
and
m represents the number 2 or 3,
or
n represents the number 0,
and
m represents the number 1,
$R^1$ represents tert-butyloxycarbonyl or (9H-fluoren-9-yl-methoxy)carbonyl,
$R^2$ represents tert-butyloxycarbonyl,
$R^3$ represents hydrogen, methyl, ethyl, n-propyl, isopropyl or benzyl,
$R^4$ represents a group of the formula

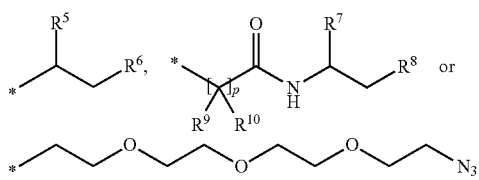

where
* is the point of attachment to the nitrogen,
p represents the number 1, 2, 3, 4 or 5,
$R^5$ represents hydrogen, aminocarbonyl, phenylaminocarbonyl or —(C=O)NHCH$_2$(C=O)NH$_2$,
$R^6$ represents —S-trityl,
$R^7$ represents hydrogen or aminocarbonyl,
$R^8$ represents —S-trityl,
$R^9$ represents hydrogen,
and
$R^{10}$ represents hydrogen.

Preference is also given to compounds of the formula (I) in which n represents the number 2 or 3,
m represents the number 0,
$R^1$ represents tert-butyloxycarbonyl or (9H-fluoren-9-yl-methoxy)carbonyl,
$R^2$ represents tert-butyloxycarbonyl,
$R^3$ represents hydrogen or methyl, R⁴ represents a group of the formula

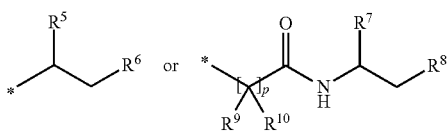

where
* is the point of attachment to the nitrogen,
p represents the number 1 or 5,
R⁵ represents hydrogen, aminocarbonyl, phenylaminocarbonyl or —(C=O)NHCH₂(C=O)NH₂,
R⁶ represents —S-trityl,
R⁷ represents hydrogen or aminocarbonyl,
R⁸ represents —S-trityl,
R⁹ represents hydrogen,
and
R¹⁰ represents hydrogen.

Preference is also given to compounds of the formula (I) in which
n represents the number 0,
m represents the number 2 or 3,
R¹ represents tert-butyloxycarbonyl or (9H-fluoren-9-ylmethoxy)carbonyl,
R² represents tert-butyloxycarbonyl,
R³ represents hydrogen or methyl,
R⁴ represents a group of the formula

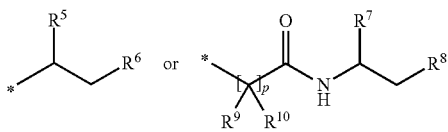

where
* is the point of attachment to the nitrogen,
p represents the number 1 or 5,
R⁵ represents hydrogen, aminocarbonyl, phenylaminocarbonyl or —(C=O)NHCH₂(C=O)NH₂,
R⁶ represents —S-trityl,
R⁷ represents hydrogen or aminocarbonyl,
R⁸ represents —S-trityl,
R⁹ represents hydrogen,
and
R¹⁰ represents hydrogen.

Preference is also given to compounds of the formula (I) in which
n represents the number 0,
m represents the number 1,
R¹ represents tert-butyloxycarbonyl or (9H-fluoren-9-ylmethoxy)carbonyl,
R² represents tert-butyloxycarbonyl,
R³ represents hydrogen or methyl,
R⁴ represents a group of the formula

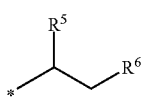

where
* is the point of attachment to the nitrogen,
R⁵ represents hydrogen, aminocarbonyl, phenylaminocarbonyl or —(C=O)NHCH₂(C=O)NH₂,
and
R⁶ represents —S-trityl.

Preference is also given to compounds of the formula (I) in which n represents the number 2 or 3 and m represents the number 0.

Preference is also given to compounds of the formula (I) in which n represents the number 2 and m represents the number 0.

Preference is also given to compounds of the formula (I) in which n represents the number 3 and m represents the number 0.

Preference is also given to compounds of the formula (I) in which n represents the number 0 and m represents the number 2 or 3.

Preference is also given to compounds of the formula (I) in which n represents the number 0 and m represents the number 1.

Preference is also given to compounds of the formula (I) in which R¹ represents tert-butyloxycarbonyl.

Preference is also given to compounds of the formula (I) in which R³ represents hydrogen or methyl.

Preference is also given to compounds of the formula (I) in which
R⁴ represents a group of the formula

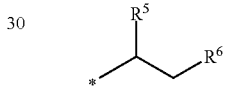

where
* is the point of attachment to the nitrogen,
R⁵ represents aminocarbonyl,
and
R⁶ represents —S-trityl.

Preference is also given to compounds of the formula (I) in which R⁶ represents —S-trityl.

Preference is also given to compounds of the formula (I) in which R⁸ represents —S-trityl.

Preference is also given to compounds of the formula (I) in which R⁹ represents hydrogen and R¹⁰ represents hydrogen.

Preference is also given to compounds of the formula (I) in which the carbon atom to which the —NHR¹ substituent is bonded has S configuration.

Preference is also given to compounds of the formula (I) which have the structure of the formula (Ia)

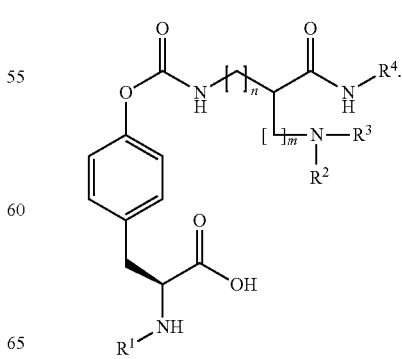

(Ia)

The specific radical definitions given in the particular combinations or preferred combinations of radicals are, irrespective of the particular combination of the radical specified, also replaced by any radical definitions of other combinations.

Very particular preference is given to combinations of two or more of the abovementioned preferred ranges.

The invention further provides a process for preparing the compounds of the formula (I), or salts thereof, solvates thereof or the solvates of salts thereof, wherein the compounds of the formula (II)

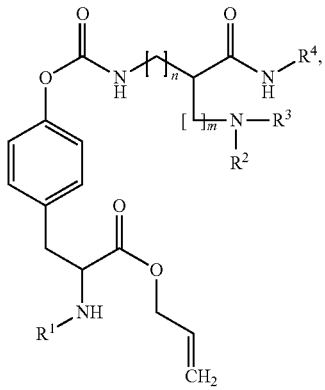

(II)

in which n, m, $R^1$, $R^2$, $R^3$ and $R^4$ are each as defined above, are reacted with a Palladium(0) source and a reducing agent.

The reaction is generally effected in inert solvents, optionally in the presents of a weak base, preferably in a temperature range of 0° C. to 50° C. at standard pressure.

Inert solvents are, for example, halohydrocarbons such as dichloromethane, trichloromethane or 1,2-dichloroethane, ethers such as dioxane, tetrahydrofuran or 1,2-dimethoxyethane, or other solvents such as acetone, dimethylformamide, dimethylacetamide, 2-butanone or acetonitrile. It is equally possible to use mixtures of the solvents. Preference is given to tetrahydrofuran.

Palladium(0) sources are, for example, tetrakis(triphenylphosphin)palladium(0), tris(dibenzylideneacetone)dipalladium(0) or Palladium(II) sources that are reduced in situ to Palladium(0) during the reaction, preference being given to tetrakis(triphenylphosphin)-palladium(0).

Reducing agents are, for example, formic acid or triethyl silane, preference being given to formic acid.

Bases are, for example, triethylamine, N,N-diisopropylethylamine or potassium phosphate solution, preference being given to triethylamine.

The compounds of the formula (II) are known or can be prepared by reacting compounds of the formula (III)

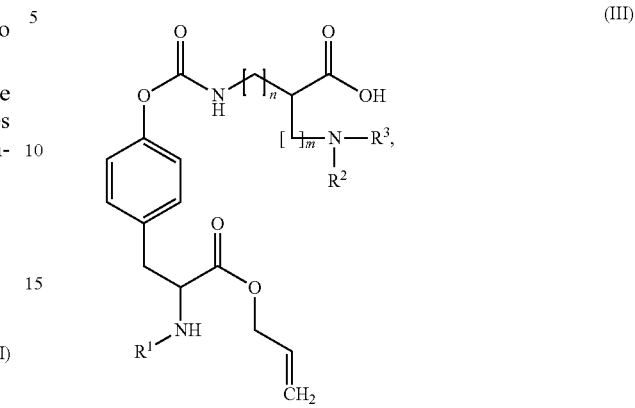

(III)

in which n, m, $R^1$, $R^2$ and $R^3$ are each as defined above, with compounds of the formula (IV)

(IV), in which $R^4$ are as defined above.

The reaction is generally effected in inert solvents, in the presence of a dehydrating reagent, optionally in the presence of a base, preferably in a temperature range from room temperature to 70° C. at standard pressure.

Inert solvents are, for example, halohydrocarbons such as dichloromethane, trichloromethane or 1,2-dichloroethane, ethers such as dioxane, tetrahydrofuran or 1,2-dimethoxyethane, or other solvents such as acetone, dimethylformamide, dimethylacetamide, 2-butanone or acetonitrile. It is equally possible to use mixtures of the solvents. Preference is given to dichloromethane.

Suitable dehydrating reagents in this context are, for example, carbodiimides, for example N,N'-diethyl-, N,N'-dipropyl-, N,N'-diisopropyl-, N,N'-dicyclohexylcarbodiimide, N-(3-dimethylaminoiso-propyl)-N'-ethylcarbodiimide hydrochloride (EDC), N-cyclohexylcarbodiimide-N'-propyloxymethyl-polystyrene (PS-carbodiimide), or carbonyl compounds such as carbonyldiimidazole, or 1,2-oxazolium compounds such as 2-ethyl-5-phenyl-1,2-oxazolium 3-sulphate or 2-tert-butyl-5-methylisoxazolium perchlorate, or acylamino compounds such as 2-ethoxy-1-ethoxycarbonyl-1,2-di-hydroquinoline, or propanephosphonic anhydride, or isobutyl chloroformate, or bis-(2-oxo-3-oxa-zolidinyl)phosphoryl chloride or benzotriazolyloxytri(dimethylamino) phosphonium hexafluorophosphate, or O-(benzotriazol-1-yl)-N,N,N',N'-tetramethyluronium hexafluorophosphate (HBTU), benzotriazol-1-yl-N-tetramethyl-uronium tetrafluoroborate (TBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or benzotriazol-1-yloxytris(pyrrolidino)phosphonium hexafluorophosphate (PYBOP), or N-hydroxysuccinimide, or mixtures of these with bases.

Bases are, for example, alkali metal carbonates, for example sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethylaminopyridine or N,N-diisopropylethylamine, preference being given to N,N-diisopropylethylamine.

Preferably, the condensation is carried out with HATU in the presence of N,N-diisopropylethylamine.

The compounds of the formula (III) and (IV) are known or can be synthesized by known processes from the appropriate starting compounds.

The preparation of the compounds according to the invention can be illustrated by the following synthesis scheme:

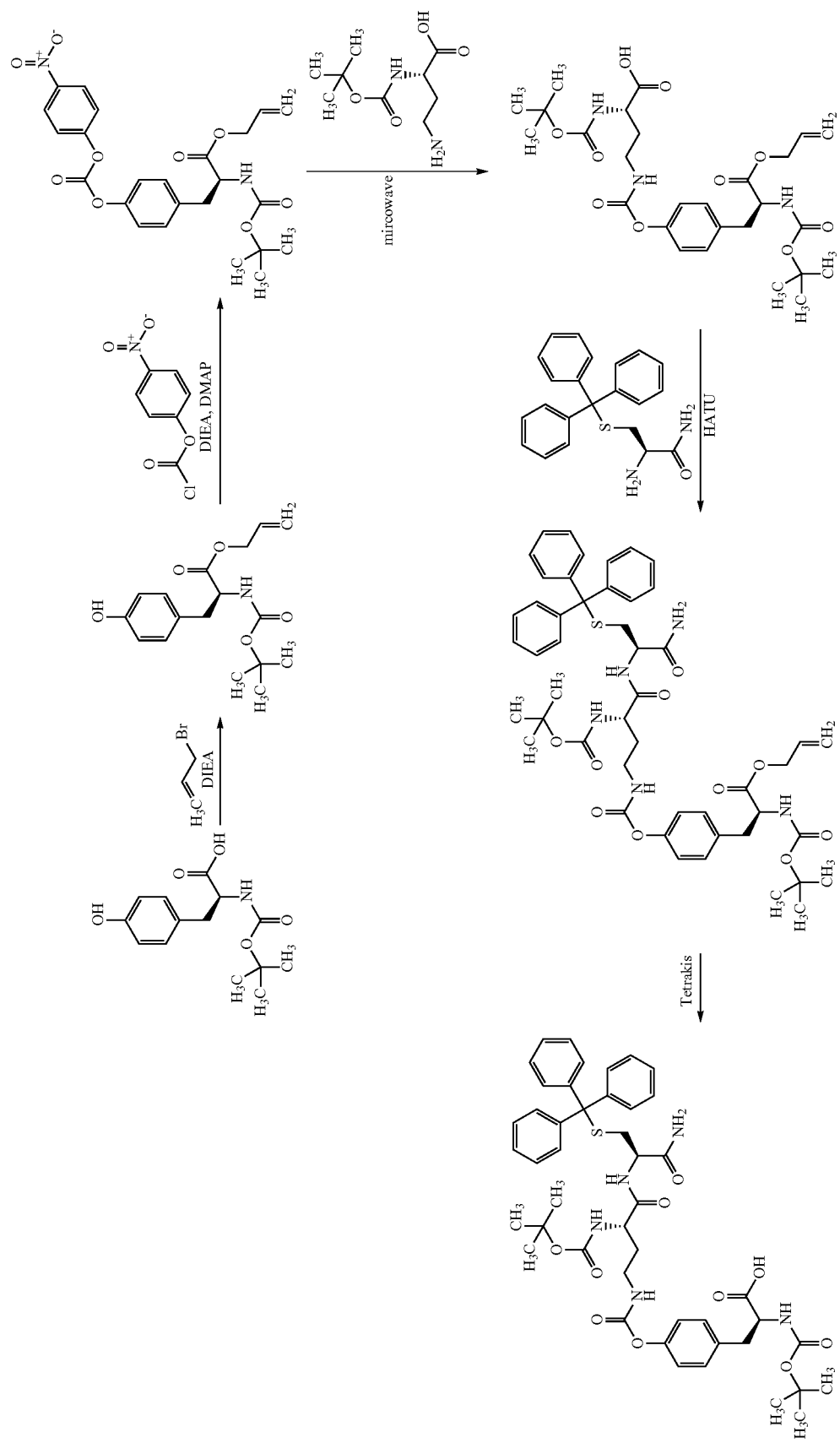
Scheme 1

The compounds according to the invention are usable as the releasable connection of peptides or proteins with other molecular entities, e.g. polyethylene glycol or other modifiers, to form a prodrug of said peptides or proteins.

The active principle of these tyrosine derivatives is a carbamate between the penolic OH-group of a tyrosine in a peptide or protein sequence and one amine functionality of a diamino acid. The second amine of the diamino acid is protonated under acidic conditions. But at neutral or basic conditions it acts as a nucleophile attacking the carbamate. This leads to the formation of a cyclic urea and release of the unmodified tyrosine. The acid functionality of the diamino acid is used as the attachment point for a modifier. Many different approaches to attach a modifier at this functionality can be envisioned. A common methodology to attach modifiers such as polyethylene glycol to a peptide is by reacting PEG-maleimides with cystein residues or other thiols. Therefore a straight forward way to achieve the desired task is the attachment of a cystein residue via its amine functionality to the carboxy group of the diaminoacid. The carboxy terminus of the cystein could be for example a primary amide but many other modifications on its C-terminus are also possible. Between the diamino acid and the cystein or any other thiol functionality, in is easily envisioned that a plethora of spacer groups would be suitable without changing the character of this linking concept since all of this molecular construct remains between the cyclic urea formed from the diamino acid on the one end and the modifier on the other end. The released peptide or protein is not changed in any way. Also the chemistry to attach modifiers to the linker is not limited to the reaction of a thiol functionality with a maleimide. Other well known methods to link modifiers such as PEG to a thiol are equally suitable. Also many other thiol free linking methodologies such as "click"-chemistry or simple amide bond formations to an amine functionalized modifier are alternatives. Scheme 2 shows an examplaric attachment of a modifier to a peptide incorporating the tyrosine based amino acid derivative.

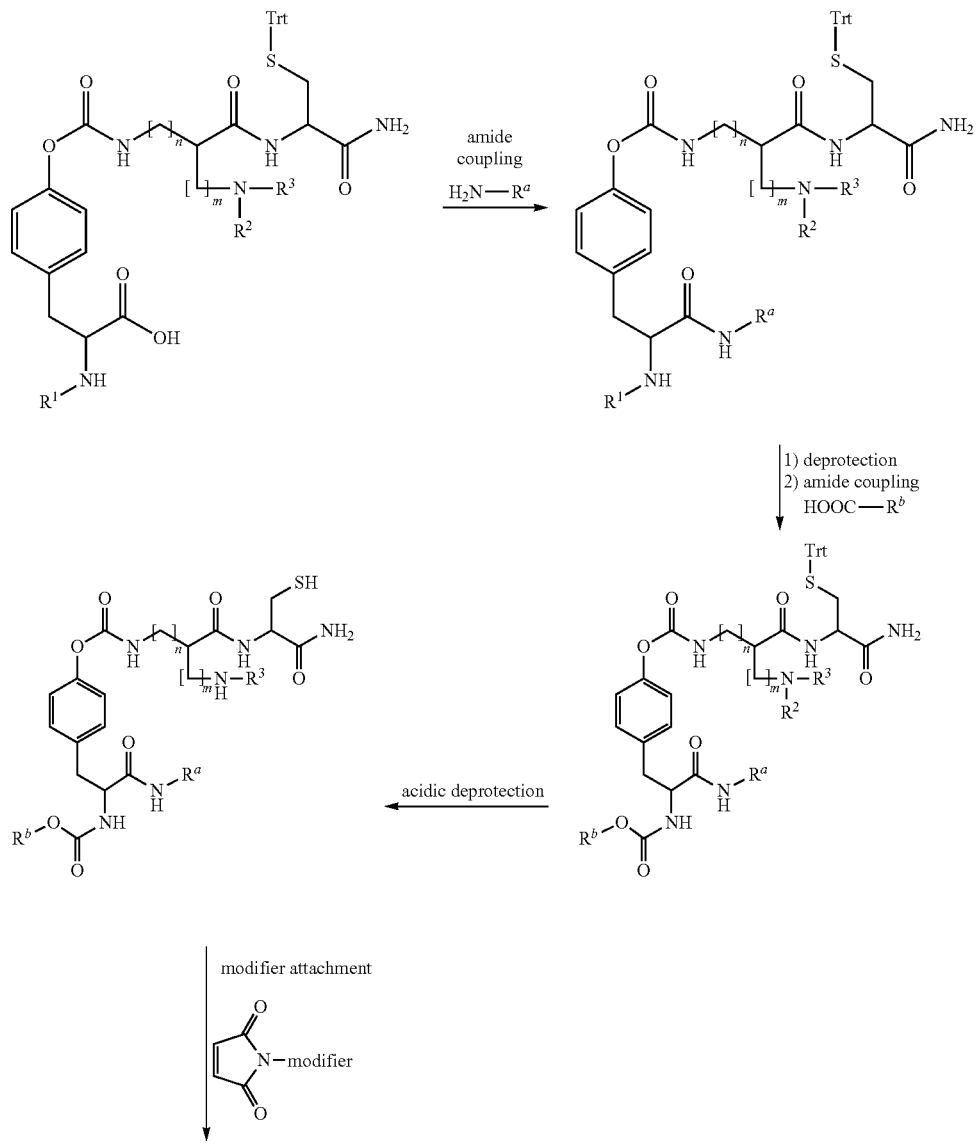

Scheme 2

-continued

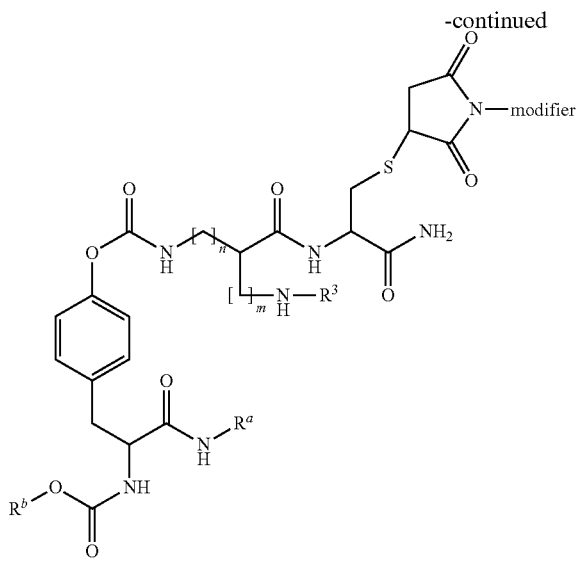

The peptides or proteins are released from said prodrug in a pH depended manner. The prodrugs are stable around pH 4 but release the active drug at physiological pH. After release of the peptide or protein form the prodrug all that is remaining in the peptide or protein is an unmodified tyrosine at the former attachment point of the linker. Therefore all peptides or proteins containing at least on tyrosine are potentially amenable to such modification.

The pH depended cleavage of the prodrug to release the peptide or protein helps to design a controlled degradation of such prodrug with predictable pharmaco kinetics.

The compounds according to the invention can be incorporated into a peptide or protein according to solution as well as solid phase peptide synthesis protocols.

Suitable proteins and peptides containing at least one thyrosine amino acid are but are not limited to adenosine deaminase, adiponectin, adrenocorticotropic hormone (ACTH), adrenomedullin (ADM), agalsidase, albumin, alfa-1 proteinase inhibitor (API), alfa-I antitrypsin b (AAT), alteplase, ancrod serine, angiotensin, angiotensinogenangiotensin, anistreplase, antimullerian hormone, antithrombin III, antitrypsins, aprotinin, asparaginases, atriopeptin, biphalin, bradykinin, calcitonin, cholecystokinin, choriogonadotropind, choriomammotropin, collagenase, corticoliberin, corticotropin, DNase, endorphins, enkephalins, enoxacin, erythropoietins, Factor II, Factor IIa, Factor IX, Factor IXa, Factor VII, Factor VIIa, Factor VIII, Factor VIIIa, Factor X, Factor Xa, Factor XI, Factor XIa, fibrinolysin, fibrinolysin, folliberin, follicle-stimulating hormones, follitropin, Fsh, galactosidase, gastrin, ghrelin, glucagon, glucagon-like peptides like (GLP-1), glucocerebrosidase, glumitocin f, gonadoliberin c, gonadotropine, gonadotropin-releasing hormone, granulocyte colony stimulating factor (G-CSF), granulocyte macrophage colony stimulating factor (GM-CSF), growth factors, growth hormone-releasing hormone, growth hormones, hemoglobins, hepatitis B vaccines, hirudin, human chorionic gonadotropin, human placental lactogen, hyaluronidases, Idarubicin, idurnonidase, immune globulins, influenza vaccines, inhibin, insulins, interferons, interleukins, isotocin g, kallidin, keratinocyte growth factor (KGF), lactase, leptin, leuprolide, levothyroxine, lipotropin, lisinopril, luliberin, luteinizing hormone, lutropin, melanocyte stimulating hormone, melanoliberin, melanostatin, melanotropinh, natriuretic peptide, orexin, orticotropin-releasing hormone, oxytocin, pancrelipase, pancreozymin, papain, parathyroid hormone, pepsin, phospholipase-activating protein (PLAP), platelet activating factor acetylhydrolase (PAF-AH), proangiotensin, prolactin, prolactoliberin, prolactostatin, proteases, protein C, relaxin, secretin, sennorelin, somatoliberin, somatomedin, somatropins, streptokinase, sucrase, superoxide dismutase (SOD), thrombopoietin, thymopoietinn, thymosin, thyroid stimulating hormone, thyroliberin, thyrotropin, thyrotropin-releasing hormone, tilactase, tissue plasminogen activator (tPA), tumor necrosis factor (TNF), urate oxidase, urogonadotropin k, urokinase, vaccines, vasopressin, vasotocin, $\alpha$-1 a antitrypsin. Mutant versions of peptides or proteins listed above or all other proteins prepared by recombinant methodologies such as antibodies, antibody fragments, single chain binding proteins and fusion proteins are also included. Also any synthetic peptide or proteins with biological activity are included.

The compounds according to the invention are suitable for use for the preparation of prodrugs which are suitable for use as medicaments for treatment and/or prevention of diseases in humans and animals.

The compounds according to the invention are suitable for use for the preparation of specific adrenomedullin (ADM) releasing prodrugs.

The present invention further provides for the use of the compounds according to the invention for the preparation of prodrugs for treatment and/or prevention of disorders.

For the present invention, the term "treatment" or "treating" includes inhibiting, delaying, relieving, mitigating, arresting, reducing, or causing the regression of a disease, disorder, condition, or state, the development and/or progression thereof, and/or the symptoms thereof. The term "prevention" or "preventing" includes reducing the risk of having, contracting, or experiencing, a disease, disorder, condition, or state, the development and/or progression thereof, and/or the symptoms thereof. The term prevention includes prophylaxis. Treatment or prevention of a disease, disorder, condition, or state may be partial or complete.

On the basis of their pharmacological properties, the prodrugs prepared with the compounds according to the invention can be employed for treatment and/or prevention of cardiovascular diseases, in particular chronic and acute heart failure, diastolic and systolic (congestive) heart failure, acute decompensated heart failure, cardiac insufficiency, coronary heart disease, angina pectoris, myocardial infarction, ischemia reperfusion injury, ischemic and hemorrhagic stroke, arteriosclerosis, atherosclerosis, essential hypertension, malignant essential hypertension, secondary hypertension, renovascular hypertension and hypertension secondary to renal and endocrine disorders, hypertensive heart disease, hypertensive renal disease, secondary pulmonary hypertension, pulmonary hypertension following pulmonary embolism with and without acute cor pulmonale, primary pulmonary hypertension, and peripheral arterial occlusive disease.

The prodrugs prepared with the compounds according to the invention are furthermore suitable for treatment and/or prevention of gestational [pregnancy-induced] edema and proteinuria with and without hypertension (pre-eclampsia).

The prodrugs prepared with the compounds according to the invention are furthermore suitable for treatment and/or prevention of pulmonary disorders, such as chronic obstructive pulmonary disease, asthma, acute and chronic pulmonary edema, allergic alveolitis and pneumonitis due to inhaled organic dust and particles of fungal, actinomycetic or other origin, acute chemical bronchitis, acute and chronic chemical pulmonary edema (e.g. after inhalation of phosgene, nitrogen oxide), neurogenic pulmonary edema, acute and chronic pulmonary manifestations due to radiation, acute and chronic interstitial lung disorders (such as but not restricted to drug-induced interstitial lung disorders, e.g. secondary to Bleomycin treatment), acute lung injury/acute respiratory distress syndrome (ALI/ARDS) in adult or child including newborn, ALI/ARDS secondary to pneumonia and sepsis, aspiration pneumonia and ALI/ARDS secondary to aspiration (such as but not restricted to aspiration pneumonia due to regurgitated gastric content), ALI/ARDS secondary to smoke gas inhalation, transfusion-related acute lung injury (TRALI), ALI/ARDS or acute pulmonary insufficiency following surgery, trauma or burns, ventilator induced lung injury (VILI), lung injury following meconium aspiration, pulmonary fibrosis, and mountain sickness.

The prodrugs prepared with the compounds according to the invention are furthermore suitable for treatment and/or prevention of chronic kidney diseases (stages 1-5), renal insufficiency, diabetic nephropathy, hypertensive chronic kidney disease, glomerulonephritis, rapidly progressive and chronic nephritic syndrome, unspecific nephritic syndrome, nephrotic syndrome, hereditary nephropathies, acute and chronic tubulo-interstitial nephritis, acute kidney injury, acute kidney failure, posttraumatic kidney failure, traumatic and postprocedural kidney injury, cardiorenal syndrome, and protection and functional improvement of kidney transplants.

The prodrugs prepared with the compounds according to the invention are moreover suitable for treatment and/or prevention of diabetes mellitus and its consecutive symptoms, such as e.g. diabetic macro- and microangiopathy, diabetic nephropathy and neuropathy.

The prodrugs prepared with the compounds according to the invention can moreover be used for treatment and/or prevention of disorders of the central and peripheral nervous system such as viral and bacterial meningitis and encephalitis (e.g. Zoster encephalitis), brain injury, primary or secondary [metastasis] malignant neoplasm of the brain and spinal cord, radiculitis and polyradiculitis, Guillain-Barre syndrome [acute (post-)infective polyneuritis, Miller Fisher Syndrome], amyotrophic lateral sclerosis [progressive spinal muscle atrophy], Parkinson's disease, acute and chronic polyneuropathies, pain, cerebral edema, Alzheimer's disease, degenerative diseases of the nervous system and demyelinating diseases of the central nervous system such as but not restricted to multiple sclerosis.

The prodrugs prepared with the compounds according to the invention are furthermore suitable for treatment and/or prevention of portal hypertension and liver fibrosis [cirrhosis] and its sequelae such as esophageal varices and ascites, for the treatment and/or prevention of pleural effusions secondary to malignancies or inflammations and for the treatment and/or prevention of lymphedema and of edema secondary to varices.

The prodrugs prepared with the compounds according to the invention are furthermore suitable for treatment and/or prevention of inflammatory disorders of the gastrointestinal tract such as inflammatory bowel disease, Crohn's disease, ulcerative colitis, and toxic and vascular disorders of the intestine.

The prodrugs prepared with the compounds according to the invention are furthermore suitable for treatment and/or prevention of sepsis, septic shock, systemic inflammatory response syndrome (SIRS) of non-infectious origin, hemorrhagic shock, sepsis or SIRS with organ dysfunction or multi organ failure (MOF), traumatic shock, toxic shock, anaphylactic shock, urticaria, insect sting and bite-related allergies, angioneurotic edema [Giant urticaria, Quincke's edema], acute laryngitis and tracheitis, and acute obstructive laryngitis [croup] and epiglottitis.

The prodrugs prepared with the compounds according to the invention are furthermore suitable for treatment and/or prevention of diseases of the rheumatic type and other disease forms to be counted as autoimmune diseases such as but not restricted to polyarthritis, lupus erythematodes, scleroderma, purpura and vasculitis.

The prodrugs prepared with the compounds according to the invention are furthermore suitable for treatment of ocular hypertension (glaucoma), diabetic retinopathy and macular edema.

The prodrugs prepared with the compounds according to the invention can moreover be used for treatment and/or prevention of operation-related states of ischemia and consecutive symptoms thereof after surgical interventions, in particular interventions on the heart using a heart-lung machine (e.g. bypass operations, heart valve implants), interventions on the carotid arteries, interventions on the aorta and interventions with instrumental opening or penetration of the skull cap.

The prodrugs prepared with the compounds are furthermore suitable for general treatment and/or prevention in the event of surgical interventions with the aim of accelerating wound healing and shortening the reconvalescence time. They are further suited for the promotion of wound healing.

The prodrugs prepared with the compounds are furthermore suitable for treatment and/or prevention of disorders of bone density and structure such as but not restricted to osteoporosis, osteomalacia and hyperparathyroidism-related bone disorders.

The prodrugs prepared with the compounds are furthermore suitable for treatment and/or prevention of sexual dysfunctions, in particular male erectile dysfunction.

Preferable the prodrugs prepared with the compounds are suitable for treatment and/or prevention of heart failure, coronary heart disease, ischemic and/or hemorrhagic stroke, hypertension, pulmonary hypertension, peripheral arterial occlusive disease, pre-eclampsia, chronic obstructive pulmonary disease, asthma, acute and/or chronic pulmonary edema, allergic alveolitis and/or pneumonitis due to inhaled organic dust and particles of fungal, actinomycetic or other origin, and/or acute chemical bronchitis, acute and/or chronic chemical pulmonary edema, neurogenic pulmonary edema, acute and/or chronic pulmonary manifestations due to radiation, acute and/or chronic interstitial lung disorders, acute lung injury/acute respiratory distress syndrome (ALI/ARDS) in adult or child including newborn, ALI/ARDS secondary to pneumonia and sepsis, aspiration pneumonia and ALI/ARDS secondary to aspiration, ALI/ARDS secondary to smoke gas inhalation, transfusion-related acute lung injury (TRALI), ALI/ARDS and/or acute pulmonary insufficiency following surgery, trauma and/or burns, and/or ventilator induced lung injury (VILI), lung injury following meconium aspiration, pulmonary fibrosis, mountain sickness, chronic kidney diseases, glomerulonephritis, acute kidney injury, cardiorenal syndrome, lymphedema, inflammatory bowel disease, sepsis, septic shock, systemic inflammatory response syndrome (SIRS) of non-infectious origin, anaphylactic shock and/or urticaria.

The present invention further provides for the use of the prodrugs prepared with the compounds according to the invention for treatment and/or prevention of disorders, in particular the disorders mentioned above.

The present invention further provides for the use of the prodrugs prepared with the compounds according to the invention for preparing a medicament for treatment and/or prevention of disorders, in particular the disorders mentioned above.

The present invention further provides a method for treatment and/or prevention of disorders, in particular the disorders mentioned above, using an active amount of the prodrugs prepared with the compounds according to the invention.

The invention further provides medicaments comprising a prodrugs prepared with the compound according to the invention and one or more further active ingredients, in particular for treatment and/or prevention of the disorders mentioned above. Exemplary and preferred active ingredient combinations are:

ACE inhibitors, angiotensin receptor antagonists, beta-2 receptor agonists, phosphodiesterase inhibitors, glucocorticoid receptor agonists, diuretics, or recombinant angiotensin converting enzyme-2 or acetylsalicylic acid (aspirin).

In a preferred embodiment of the invention, the prodrugs prepared with the compounds according to the invention are administered in combination with an ACE inhibitor, such as, by way of example and preferably, enalapril, quinapril, captopril, lisinopril, ramipril, delapril, fosinopril, perindopril, cilazapril, imidapril, benazepril, moexipril, spirapril or trandopril.

In a preferred embodiment of the invention, the prodrugs prepared with the compounds according to the invention are administered in combination with an angiotensin receptor antagonist, such as, by way of example and preferably, losartan, candesartan, valsartan, telmisartan or embusartan.

In a preferred embodiment of the invention, the prodrugs prepared with the compounds according to the invention are administered in combination with a beta-2 receptor agonist, such as, by way of example and preferably, salbutamol, pirbuterol, salmeterol, terbutalin, fenoterol, tulobuterol, clenbuterol, reproterol or formoterol.

In a preferred embodiment of the invention, the prodrugs prepared with the compounds according to the invention are administered in combination with a phosphodiesterase (PDE) inhibitor, such as, by way of example and preferably, milrinone, amrinone, pimobendan, cilostazol, sildenafil, vardenafil or tadalafil.

In a preferred embodiment of the invention, the prodrugs prepared with the compounds according to the invention are administered in combination with a glucocorticoid receptor agonist, such as, by way of example and preferably, cortiosol, cortisone, hydrocortisone, prednisone, methyl-prednisolone, prednylidene, deflazacort, fluocortolone, triamcinolone, dexamethasone or betamethasone.

In a preferred embodiment of the invention, the prodrugs prepared with the compounds according to the invention are administered in combination with diuretics, such as, by way of example and preferably, furosemide, torasemide and hydrochlorothiazide.

The present invention further relates to medicaments which comprise at least one prodrug prepared with a compound according to the invention, normally together with one or more inert, nontoxic, pharmaceutically suitable excipients, and to the use thereof for the aforementioned purposes.

The prodrugs prepared with the compounds according to the invention can act systemically and/or locally. For this purpose, they can be administered in a suitable way, for example by the parenteral, pulmonary, nasal, sublingual, lingual, buccal, dermal, transdermal, conjunctival, optic route or as implant or stent.

The prodrugs prepared with the compounds according to the invention can be administered in administration forms suitable for these administration routes.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration include preparations for injection and infusion in the form of solutions, suspensions, emulsions, lyophilizates or sterile powders.

Suitable for the other administration routes are, for example, pharmaceutical forms for inhalation (including powder inhalers, nebulizers), nasal drops, eye drops, solutions or sprays; films/wafers or aqueous suspensions (lotions, shaking mixtures), lipophilic suspensions, ointments, creams, transdermal therapeutic systems (e.g. patches), milk, pastes, foams, dusting powders, implants or stents.

Parenteral administration is preferred, especially intravenous administration.

The prodrugs prepared with the compounds according to the invention can be converted into the stated administration forms. This can take place in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersants or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colors (e.g. inorganic pigments, for example iron oxides) and masking flavors and/or odors.

It has generally been found to be advantageous, in the case of parenteral administration, to administer amounts of about 0.001 to 5 mg/kg, preferably about 0.01 to 1 mg/kg, of body weight to achieve effective results.

It may nevertheless be necessary in some cases to deviate from the stated amounts, in particular as a function of the body weight, route of administration, individual response to the active ingredient, nature of the preparation and time or interval over which administration takes place. For instance, less than the aforementioned minimum amount may be sufficient in some cases, whereas in other cases the stated upper limit must be exceeded. In the case of administration of larger amounts, it may be advisable to divide these into a plurality of individual doses over the day.

The following working examples illustrate the invention. The invention is not restricted to the examples.

The percentages in the following tests and examples are, unless stated otherwise, percentages by weight; parts are parts by weight. Solvent ratios, dilution ratios and concentration data for the liquid/liquid solutions are each based on volume.

A. EXAMPLES

Abbreviations

AA amino acid
Acm acetamidomethyl
approx. approximately
Boc tert-butyloxycarbonyl
CDI carbonyldiimidazole
d day(s), doublet (in NMR)
TLC thin-layer chromatography
DCI direct chemical ionization (in MS)
dd doublet of doublets (in NMR)
DIEA N,N-diisopropylethylamine
DMAP 4-dimethylaminopyridine
DMF N,N-dimethylformamide
DMSO dimethyl sulfoxide
of theory of theory (in yield)
eq. equivalent(s)
ESI electrospray ionization (in MS)
Fmoc (9H-fluoren-9-ylmethoxy)carbonyl
h hour(s)
HATU O-(7-azabenzotriazol-1-yl)-N,N,N',N'-tetramethyluronium hexafluorophosphate
HPLC high pressure, high performance liquid chromatography
LC-MS liquid chromatography-coupled mass spectroscopy
m multiplet (in NMR)
min minute(s)
MS mass spectroscopy
NMR nuclear magnetic resonance spectroscopy
RP reversed phase (in HPLC)
RT room temperature
$R_t$ retention time (in HPLC)
s singulet (in NMR)
TBTU benzotriazol-1-yl-N-tetramethyl-uronium tetrafluoroborate
tBu tert-butyl
TFA trifluoroacetic acid
THF tetrahydrofuran
Trt trityl
LC-MS and MS Methods
Method 1 (LC-MS):
Instrument type: Waters ACQUITY SQD UPLC System; column: Waters Acquity UPLC HSS T3 1.8µ 50 mm×1 mm; mobile phase A: 1 l water+0.25 ml 99% strength formic acid, mobile phase B: 1 l acetonitrile+0.25 ml 99% strength formic acid; gradient: 0.0 min 90% A→1.2 min 5% A→2.0 min 5% A; oven: 50° C.; flow: 0.40 ml/min; UV-detection: 210-400 nm.
Method 2 (LC-MS):
MS instrument: type: Waters (Micromass) Quattro Micro; HPLC instrument type: Agilent 1100 series; column: Thermo Hypersil GOLD 3µ 20 mm×4 mm; mobile phase A: 1 l water+0.5 ml 50% strength formic acid, mobile phase B: 1 l acetonitrile+0.5 ml 50% strength formic acid; gradient: 0.0 min 100% A→3.0 min 10% A→4.0 min 10% A; oven: 50° C.; flow: 2.0 ml/min; UV-detection: 210 nm.

Method 3 (HPLC):
Instrument type: HP 1200 Series; UV DAD; column: Phenomenex Luna 5 µm C5 100 Å, 150 mm×4.6 mm; mobile phase A: 1 l water+0.5 ml 50% strength formic acid, mobile phase B: 1 l acetonitrile+0.5 ml 50% strength formic acid; gradient: 0.0 min 95% A→5 min 5% A; →5.8 min 95% A→6.2 min 95% A; flow rate: 2.5 ml/min; oven: RT; UV detection: 210 nm.
Method 4 (HPLC):
Instrument type: HP 1200 Series; UV DAD; column: Merck Chromolith Fastgradient RP18 50 mm×2 mm; mobile phase A: 1 l water+0.5 ml 50% strength formic acid, mobile phase B: 1 l acetonitrile+0.5 ml 50% strength formic acid; gradient: 0.0 min 95% A→2.9 min 5% A→3.2 min 5% A; flow rate: 3 ml/min; oven: RT; UV detection: 210 nm.
Microwave Synthesizer:
Biotage Emrys Initiator II synthesizer, with variable vial size up to 20 ml reaction volume and "Robot 60" sample processor
pH 4 Citrate Buffer:
Fluka No 82566; Citrate buffer pH 4, stabilized with sodium azide composition: citric acid, ~0.056 M; sodium azide, ~0.05%; sodium chloride, ~0.044 M; sodium hydroxide, ~0.068 M.

Starting Compounds

Example 1A

Allyl-N-(tert-butoxycarbonyl)-O-[(4-nitrophenoxy)carbonyl]-L-tyrosinate

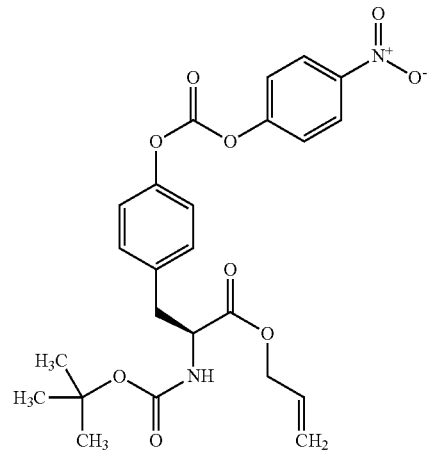 [SMILES: C=CCOC(=O)[C@H](Cc1ccc(OC(=O)Oc2ccc([N+](=O)[O-])cc2)cc1)NC(=O)OC(C)(C)C]

36.7 g (114.3 mmol) N-Boc-L-tyrosine allyl ester, 23.0 g (114.3 mmol) 4-nitrophenyl chloroformate, 17.5 ml (125.7 mmol) triethylamine and 1.40 g (11.4 mmol) 4-dimethylamino pyridine were combined in 1000 ml dichloromethane and stirred at room temperature for 2 h. The reaction mixture was extracted with approx. 500 ml water and with approx. 250 ml brine and dried over approx. 100 g sodium sulfate. The solvent was removed by rotary evaporation (approx. 40° C., approx. 200 mbar, approx. 30 min.) and the product was dissolved in warm diethyl ether and crystallized over night at 4° C. The crystals were filtered of, washed with cold diethyl ether and dried in high vacuum (approx. 0.1 mbar, 18 h). The yield was 29.86 g, (59.6 mmol, 52% of theory) of the desired product.

LC-MS (method 1): $R_t$=1.23 min., m/z=487 (M+H)$^+$

Example 2A (2S)-4-{[(4-{(2S)-3-(Allyloxy)-2-[(tert-butoxycarbonyl)amino]-3-oxopropyl}phenoxy)carbonyl]-amino}-2-[(tert-butoxycarbonyl)amino]butanoic acid

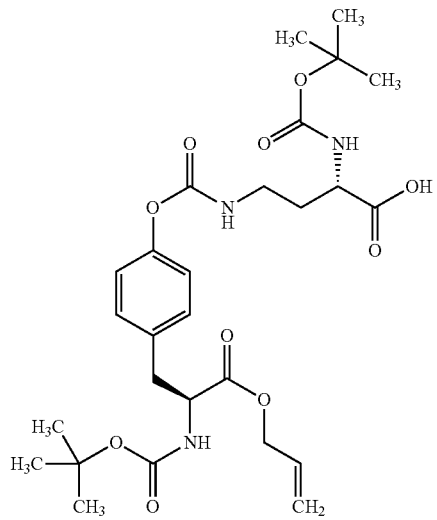 [SMILES: C=CCOC(=O)[C@H](Cc1ccc(OC(=O)NCC[C@H](NC(=O)OC(C)(C)C)C(=O)O)cc1)NC(=O)OC(C)(C)C]

4.0 g (8.22 mmol) of the compound from example 1A was dissolved in 60 ml dichloromethane. 1.795 (8.22 mmol) (2S)-4-Amino-2-[(tert-butoxycarbonyl)amino]butanoic acid and 1.43 ml (8.22 mmol) N,N-diisopropylethylamine were added. The reaction mixture was split into 3 portions. The portions were heated for 30 min in a sealed tube at 75° C. in a microwave synthesizer. From the combined reaction mixture the solvent was removed by rotary evaporation (approx. 40° C., approx. 200 mbar, approx. 30 min.). The raw product was dissolved in dichloromethane and chromatographed over approx. 600 ml silica gel. Solvents used were dichloromethane/ethyl acetate 4/1, dichloromethane/ethyl acetate 1/1, dichloromethane/methanol 4/1 and dichloromethane/methanol 1/1. The product-containing fractions were combined and concentrated to dryness under reduced pressure. This gave 4.02 g (6.54 mmol, 80% of theory) of the desired product.

LC-MS (method 1): $R_t$=1.07 min., m/z=564 (M−H)⁻

Example 3A

Allyl O-({(3S)-4-{[(2R)-1-amino-1-oxo-3-(tritylsulfanyl)propan-2-yl]amino}-3-[(tert-butoxy-carbonyl)amino]-4-oxobutyl}carbamoyl)-N-(tert-butoxycarbonyl)-L-tyrosinate

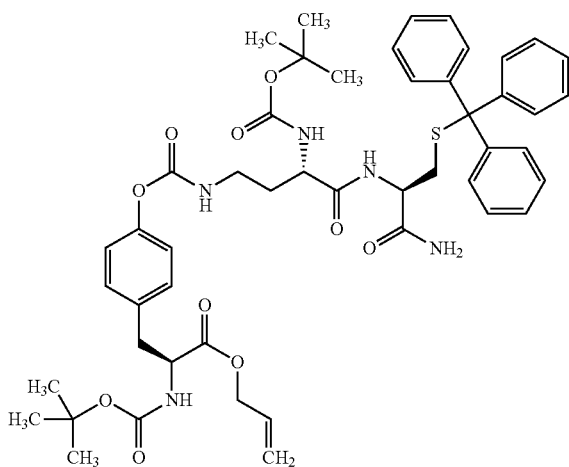 [SMILES: C=CCOC(=O)[C@H](Cc1ccc(OC(=O)NCC[C@H](NC(=O)OC(C)(C)C)C(=O)N[C@@H](CSC(c2ccccc2)(c2ccccc2)c2ccccc2)C(N)=O)cc1)NC(=O)OC(C)(C)C]

2.50 g (4.42 mmol) of the compound from example 2A was dissolved in 100 ml dichloromethane. 1.602 g (4.42 mmol) S-Trityl-L-cysteinamide, 0.77 ml (4.42 mmol) N,N-diisopropylethylamine and 1.68 g (4.42 mmol) HATU were added. The reaction mixture was split into 5 portions. The portions were heated for 30 min in a sealed tube at 60° C. in a microwave synthesizer. From the combined reaction mixture the solvent was removed by rotary evaporation (approx. 40° C., approx. 200 mbar, approx. 30 min.). The raw product was dissolved in dichloromethane and chromatographed over approx. 600 ml silica gel. Solvents used were dichloromethane/ethyl acetate 2/1, dichloromethane/ethyl acetate 1/1, dichloromethane/methanol 20/1 and dichloromethane/methanol 10/1. The product-containing fractions were combined and concentrated to dryness under reduced pressure. This gave 4.12 g (3.30 mmol, 75% of theory, 73% purity) of the desired product.

LC-MS (method 1): $R_t$=1.36 min., m/z=911 (M+H)⁺

Example 4A tert-Butyl-methyl(2-oxotetrahydrofuran-3-yl)carbamate

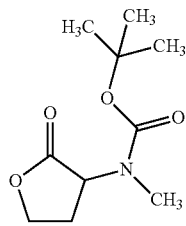

The compound was synthesized according to Alberico, Dino; Paquin, Jean-Francois; Lautens, Mark; Tetrahedron, 2005, vol. 61, p. 6283-6297.

5.18 g (25.7 mmol) tert-Butyl(tetrahydro-2-oxo-3-furanyl) carbamate, 4.81 ml (77.2 mmol) iodomethane were dissolved in 100 ml of dry dimethyl fomamide. The solution was cooled to 0° C. and 1.34 g (60% in mineral oil, 33.5 mmol) sodium hydride was added. The reaction was warmed to room temperature and stirred over night. The reaction mixture was added to approx. 400 ml water and the mixture was extracted three times with approx. 300 ml ethyl acetate. The combined organic phases were dried over sodium sulfate and concentrated to dryness under reduced pressure. This gave 8.70 g (25.7 mmol, 100% of theory, 63% purity) of the desired product.

The analytic data was in accordance with the literature. The product was used in the next synthetic step without further purification.

Example 5A

2-[(tert-Butoxycarbonyl)(methyl)amino]-4-(1,3-dioxo-1,3-dihydro-2H-isoindol-2-yl)butanoic acid

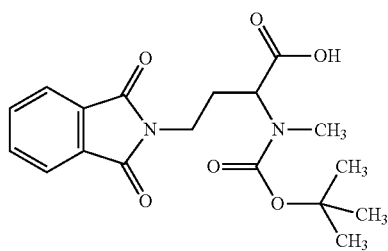 [SMILES: CN(C(=O)OC(C)(C)C)C(CCN1C(=O)c2ccccc2C1=O)C(=O)O]

8.70 g (approx. 25 mmol, approx. 63% purity) of the compound from example 4A was dissolved in 560 ml dimethyl formamide. 8.23 g (44.4 mmol) potassium ophtalimide were added and the reaction mixture was heated to 150° C. for 7 h. Approx. 400 ml of the solvent was removed by rotary evaporation (approx. 60° C., approx. 10 mbar, approx. 30 min.). The reaction mixture was poured onto a mixture of approx. 100 ml water, 200 g ice and 15 ml acetic acid. After melting of the remaining ice the reaction mixture was filtered and the filtrate was extracted 3 times with approx. 100 ml dichloromethane. The combined organic phases were dried over sodium sulfate and concentrated to dryness under reduced pressure. The raw product was dissolved in dichloromethane and chromatographed over approx. 70 ml silica gel. Solvents used were dichloromethane/ethyl acetate 9/1 to dichloromethane/ethyl acetate 6/4. The product-containing fractions were combined and concentrated to dryness under reduced pressure. This gave 2.39 g (6.04 mmol, 24% of theory) product.

LC-MS (method 1): $R_t$=0.92 min., m/z=363 (M+H)$^+$

Example 6A

4-Amino-2-[(tert-butoxycarbonyl)(methyl)amino]butanoic acid

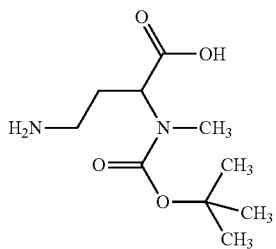

11.8 g (32.6 mmol) of the compound from example 5A was dissolved in approx. 640 ml ethanol and 23.8 ml (488 mmol) hydrazine hydrate was added to the reaction mixture. After stirring over night, the reaction mixture was filtered and the filtrate was concentrated to dryness under reduced pressure. The raw product was dissolved in ethanol and approx. 50 g silica gel was added, the solvent was removed under reduced pressure. The resulting solid was added onto a approx. 500 g silica gel column and chromatographed. Solvents used were dichloromethane/methanol 9/1 to dichloromethane/methanol 1/1. The product-containing fractions were combined and concentrated to dryness under reduced pressure. This gave 2.98 g (12.8 mmol, 39% of theory) product.

LC-MS (method 2): $R_t$=0.21 min., m/z=233 (M+H)$^+$

DCI MS (method 5): m/z=233 (M+H)$^+$

Example 7A

4-{[(4-{(2S)-3-(Allyloxy)-2-[(tert-butoxycarbonyl)amino]-3-oxopropyl}phenoxy)carbonyl]-amino}-2-[(tert-butoxycarbonyl)(methyl)amino]butanoic acid

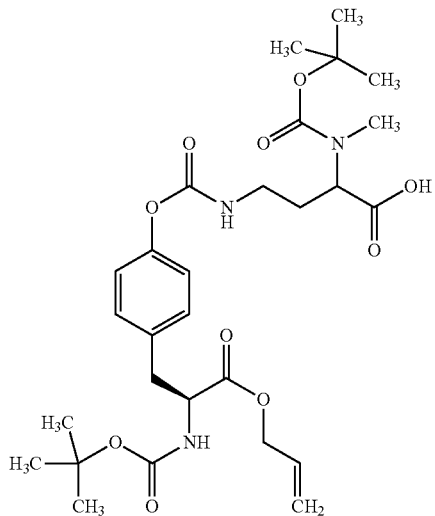 [SMILES: C=CCOC(=O)[C@H](Cc1ccc(OC(=O)NCCC(C(=O)O)N(C)C(=O)OC(C)(C)C)cc1)NC(=O)OC(C)(C)C]

0.931 g (1.92 mmol) of the compound from example 1A was dissolved in 30 ml dichloromethane. 0.455 g (1.92 mmol) of the compound from example 6A was added. The reaction mixture was split into 2 portions. The portions were heated for 30 min in a sealed tube at 80° C. in a microwave synthesizer. From the combined reaction mixture the solvent was removed under reduced pressure. The raw product was purified by preparative RP-HPLC on a C18 column with a water methanol gradient from 9/1 to 1/9. The product-containing fractions were combined and concentrated to dryness under reduced pressure. This gave 0.523 g (0.85 mmol, 44% of theory) of the desired product as a mixture of 2 diastereomers.

LC-MS (method 1): $R_t$=1.08 and 1.11 min., m/z=578 (M−H)$^-$

Example 8A

Allyl-O-[(4-{[(2R)-1-amino-1-oxo-3-(tritylsulfanyl)propan-2-yl]amino}-3-[(tert-butoxycarbonyl)-(methyl)amino]-4-oxobutyl)carbamoyl]-N-(tert-butoxycarbonyl)-L-tyrosinate

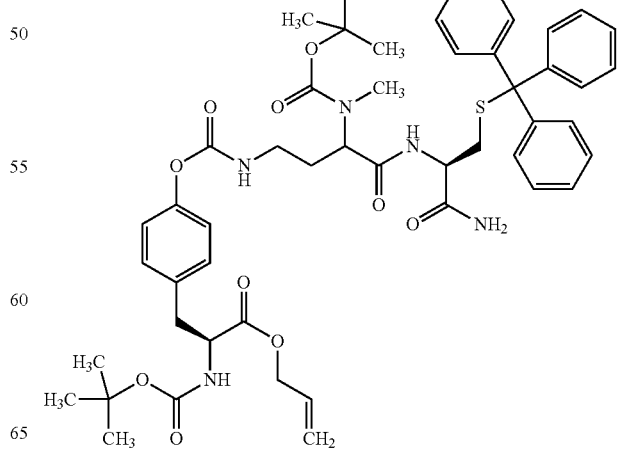

2.24 g (3.86 mmol) of the compound from example 7A was dissolved in 100 ml dichloromethane. 1.401 g (3.86 mmol) S-Trityl-L-cysteinamide, 0.67 ml (3.86 mmol) N,N-diisopropylethylamine and 1.47 g (3.86 mmol) HATU were added. The reaction mixture was split into 5 portions. The portions were heated for 30 min in a sealed tube at 60° C. in a microwave synthesizer. From the combined reaction mixture the solvent was removed by rotary evaporation (approx. 40° C., approx. 200 mbar, approx. 30 min.). The raw product was purified by preparative RP-HPLC on a C18 column with a water methanol gradient from 9/1 to 1/9. The product-containing fractions were combined and concentrated to dryness under reduced pressure. This gave 3.26 g (2.75 mmol, 71% of theory, 78% purity) of the desired product as a mixture of diastereomers.

LC-MS (method 1): $R_t$=1.41 and 1.43 min., m/z=924 (M+H)$^+$

Example 9A $N^5$-[(4-{(2S)-3-(Allyloxy)-2-[(tert-butoxycarbonyl)amino]-3-oxopropyl}phenoxy)carbonyl]-$N^2$-(tert-butoxycarbonyl)-L-ornithine

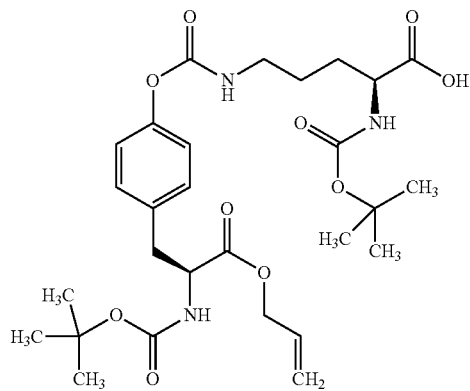 [SMILES: C=CCOC(=O)[C@H](Cc1ccc(OC(=O)NCCC[C@H](NC(=O)OC(C)(C)C)C(=O)O)cc1)NC(=O)OC(C)(C)C]

6.00 g (12.33 mmol) of the compound from example 1A was dissolved in 120 ml dichloromethane. 2.57 g (12.33 mmol) $N^2$-(tert-Butoxycarbonyl)-L-ornithine was added. The reaction mixture was split into 6 portions. The portions were heated for 90 min in a sealed tube at 75° C. in a microwave synthesizer. The combined reaction mixture was extracted with approx. 100 ml saturated ammonium chloride solution. The aqueous phase was twice back extracted with approx. 30 ml dichloromethane each. The combined organic phases were extracted with approx. 50 ml brine and dried over sodium sulfate. The solvent was removed under reduced pressure. The raw product was dissolved in dichloromethane and chromatographed over approx. 600 ml silica gel. Solvents used were dichloromethane, dichloromethane/methanol 40/1 to dichloromethane/methanol 1/1. The product-containing fractions were combined and concentrated to dryness under reduced pressure. This gave 2.63 g (4.06 mmol, 33% of theory, 89% purity) of the desired product.

LC-MS (method 1): $R_t$=1.03 min., m/z=578 (M−H)$^−$

Example 10A $N^5$-[(4-{(2S)-3-(Allyloxy)-2-[(tert-butoxycarbonyl)amino]-3-oxopropyl}phenoxy)carbonyl]-$N^2$-(tert-butoxycarbonyl)-L-ornithyl-S-trityl-L-cysteinamide

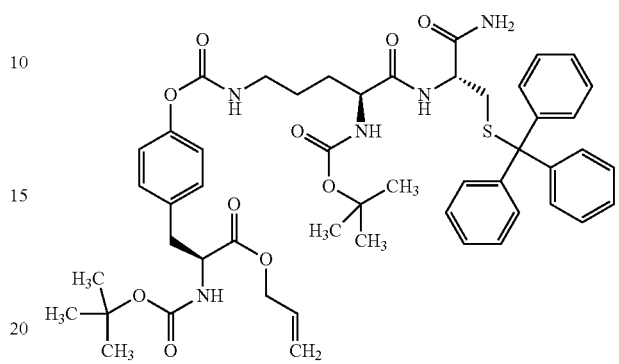

1.20 g (2.07 mmol) of the compound from example 9A was dissolved in 48 ml dichloromethane. 0.750 g (2.07 mmol) S-Trityl-L-cysteinamide, 0.36 ml (2.07 mmol) N,N-diisopropylethylamine and 0.787 g (2.07 mmol) HATU were added. The reaction mixture was split into 3 portions. The portions were heated for 30 min in a sealed tube at 60° C. in a microwave synthesizer. From the combined reaction mixture the solvent was removed by rotary evaporation (approx. 40° C., approx. 200 mbar, approx. 30 min.). The raw product was dissolved in dichloromethane and chromatographed over approx. 400 ml silica gel. Solvents used were dichloromethane/ethyl acetate 2/1, dichloromethane/ethyl acetate 1/1. The product-containing fractions were combined and concentrated to dryness under reduced pressure. This gave 1.30 g (1.5 mmol, 56% of theory, 82% purity) of the desired product.

LC-MS (method 1): $R_t$=1.35 min., m/z=924 (M+H)$^+$

Example 11A $N^2$-[(4-{(2S)-3-(Allyloxy)-2-[(tert-butoxycarbonyl)amino]-3-oxopropyl}phenoxy)carbonyl]-$N^5$-(tert-butoxycarbonyl)ornithine

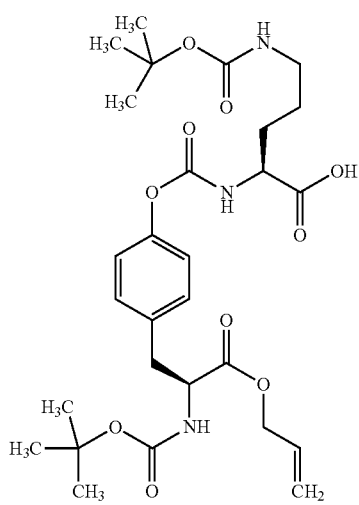 [SMILES: C=CCOC(=O)[C@H](Cc1ccc(OC(=O)N[C@@H](CCCNC(=O)OC(C)(C)C)C(=O)O)cc1)NC(=O)OC(C)(C)C]

3.00 g (6.16 mmol) of the compound from example 1A was dissolved in 60 ml dichloromethane. 1.43 g (6.16 mmol) N⁵-(tert-Butoxycarbonyl)-L-ornithine was added. The reaction mixture was split into 3 portions. The portions were heated for 30 min in a sealed tube at 75° C. in a microwave synthesizer. The combined reaction mixture was extracted with approx. 500 ml saturated ammonium chloride solution. The aqueous phase was twice back extracted with approx. 30 ml dichloromethane each. The combined organic phases were extracted with approx. 50 ml brine and dried over sodium sulfate. The solvent was removed under reduced pressure. The raw product was dissolved in dichloromethane and chromatographed over approx. 500 ml silica gel. Solvents used were dichloromethane, dichloromethane/methanol 20/1 to dichloromethane/methanol 1/1. The product-containing fractions were combined and concentrated to dryness under reduced pressure. This gave 2.29 g (3.50 mmol, 57% of theory, 89% purity) of the desired product.

LC-MS (method 1): $R_t$=1.07 min., m/z=578 (M–H)⁻

Example 12A

N²-[(4-{(2S)-3-(Allyloxy)-2-[(tert-butoxycarbonyl)amino]-3-oxopropyl}phenoxy)carbonyl]-N⁵-(tert-butoxycarbonyl)-L-ornithyl-S-trityl-L-cysteinamide

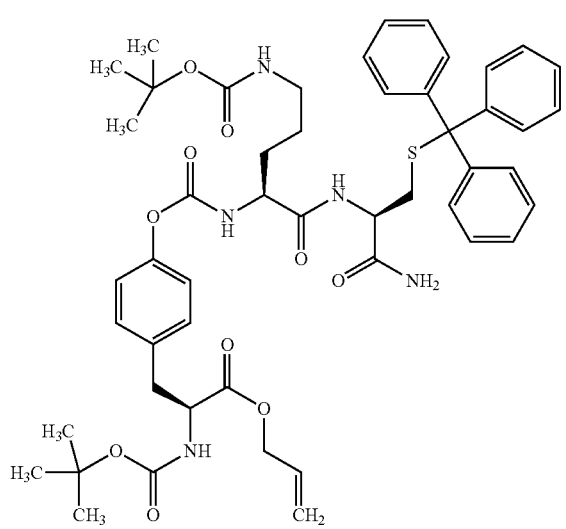 [SMILES: C=CCOC(=O)[C@H](Cc1ccc(OC(=O)N[C@@H](CCCNC(=O)OC(C)(C)C)C(=O)N[C@@H](CSC(c2ccccc2)(c2ccccc2)c2ccccc2)C(N)=O)cc1)NC(=O)OC(C)(C)C]

1.50 g (2.59 mmol) of the compound from example 11A was dissolved in 60 ml dichloromethane. 0.940 g (2.59 mmol) S-Trityl-L-cysteinamide, 0.45 ml (2.60 mmol) N,N-diisopropylethylamine and 0.984 g (2.59 mmol) HATU were added. The reaction mixture was split into 3 portions. The portions were heated for 30 min in a sealed tube at 60° C. in a microwave synthesizer. From the combined reaction mixture the solvent was removed by rotary evaporation (approx. 40° C., approx. 200 mbar, approx. 30 min.). The raw product was dissolved in dichloromethane and chromatographed over approx. 400 ml silica gel. Solvents used were dichloromethane/ethyl acetate 2/1, dichloromethane/ethyl acetate 1/1. The product-containing fractions were combined and concentrated to dryness under reduced pressure. This gave 1.72 g (1.64 mmol, 63% of theory, 88% purity) of the desired product.

LC-MS (method 1): $R_t$=1.35 min., m/z=924 (M+H)⁺

Example 13A (2S)-2-{[(4-{(2S)-3-(Allyloxy)-2-[(tert-butoxycarbonyl)amino]-3-oxopropyl}phenoxy)carbonyl]amino}-4-[(tert-butoxycarbonyl)amino]butanoic acid 7.50 g (15.4 mmol) of the compound from example 1A was dissolved in 150 ml dichloromethane. 3.36 g (15.4 mmol) (2S)-2-Amino-4-[(tert-butoxycarbonyl)amino]butanoic acid was added. The reaction mixture was split into 10 portions. The portions were heated for 30 min in a sealed tube at 75° C. in a microwave synthesizer. The combined reaction mixture was extracted with approx. 100 ml saturated ammonium chloride solution. The aqueous phase was twice back extracted with approx. 50 ml dichloromethane each. The combined organic phases were extracted with approx. 50 ml brine and dried over sodium sulfate. The solvent was removed under reduced pressure. The raw product was dissolved in dichloromethane and chromatographed over approx. 1 l silica gel. Solvents used were dicloromethane/ethyl acetate 4/1, dichloromethane/methanol 10/1 to dichloromethane/methanol 1/1. The product-containing fractions were combined and concentrated to dryness under reduced pressure. This gave 8.70 g (10.8 mmol, 70% of theory) of the desired product.

LC-MS (method 1): $R_t$=1.06 min., m/z=564 (M–H)⁻

Example 14A

Allyl-N-(tert-butoxycarbonyl)-O-{[(4R,7S)-4-carbamoyl-13,13-dimethyl-6,11-dioxo-1,1,1-triphenyl-12-oxa-2-thia-5,10-diazatetradecan-7-yl]carbamoyl}-L-tyrosinate

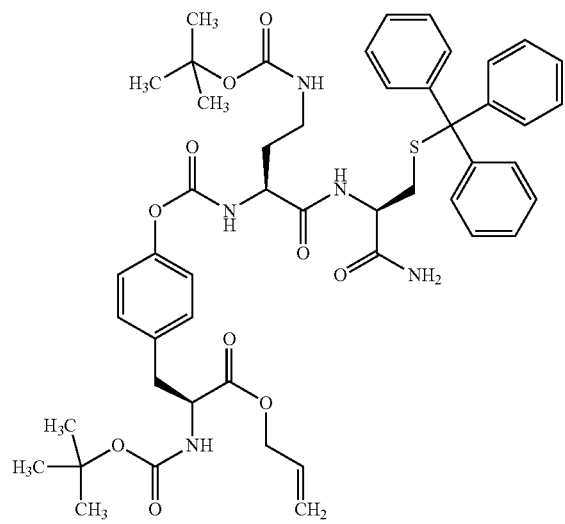 [SMILES: C=CCOC(=O)[C@H](Cc1ccc(OC(=O)N[C@@H](CCNC(=O)OC(C)(C)C)C(=O)N[C@@H](CSC(c2ccccc2)(c2ccccc2)c2ccccc2)C(N)=O)cc1)NC(=O)OC(C)(C)C]

3.00 g (5.30 mmol) of the compound from example 13A was dissolved in 120 ml dichloromethane. 1.92 g (5.30 mmol) S-Trityl-L-cysteinamide, 0.92 ml (5.30 mmol) N,N-diisopropylethylamine and 2.02 g (5.30 mmol) HATU were added. The reaction mixture was split into 6 portions. The portions were heated for 30 min in a sealed tube at 60° C. in a microwave synthesizer. From the combined reaction mixture the solvent was removed by rotary evaporation (approx. 40° C., approx. 200 mbar, approx. 30 min.). The raw product was dissolved in dichloromethane and chromatographed over approx. 800 ml silica gel. Solvents used were dichloromethane/ethyl acetate 2/1, dichloromethane/ethyl acetate 1/1. The product-containing fractions were combined and concentrated to dryness under reduced pressure. This gave 4.91 g (3.73 mmol, 70% of theory, 69% purity) of the desired product.

LC-MS (method 1): $R_t$=1.35 min., m/z=910 (M+H)$^+$

Example 15A

Allyl-N-(tert-butoxycarbonyl)-O-{[(3S)-3-[(tert-butoxycarbonyl)amino]-4-oxo-4-{[2-(tritylsulfanyl)ethyl]amino}butyl]carbamoyl}-L-tyrosinate

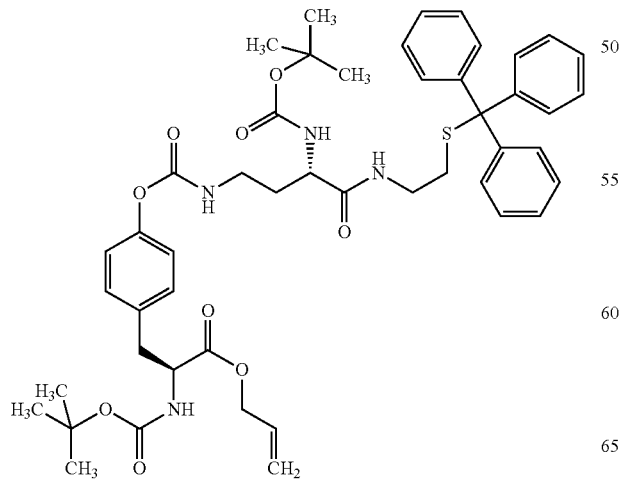

351 mg (0.63 mmol) of the compound from example 2A was dissolved in 15 ml dichloromethane. 200 mg (0.63 mmol) 2-(Tritylsulfanyl)ethanamine, 0.11 ml (0.63 mmol) N,N-diisopropylethyl-amine and 238 mg (0.63 mmol) HATU were added. The reaction mixture was heated for 30 min in a sealed tube at 60° C. in a microwave synthesizer. From the reaction mixture the solvent was removed under reduced pressure. The raw product was purified by preparative RP-HPLC on a C18 column with a water methanol gradient from 9/1 to 1/9. The product-containing fractions were combined and concentrated to dryness under reduced pressure. This gave 98 mg (0.110 mmol, 16% of theory) of the desired product.

LC-MS (method 1): $R_t$=1.45 min., m/z=867 (M+H)$^+$

Example 16A

N-{(2S)-4-{[(4-{(2S)-3-(Allyloxy)-2-[(tert-butoxycarbonyl)amino]-3-oxopropyl}phenoxy)-carbonyl]amino}-2-[(tert-butoxycarbonyl)amino]butanoyl}-S-trityl-L-cysteinylglycinamide

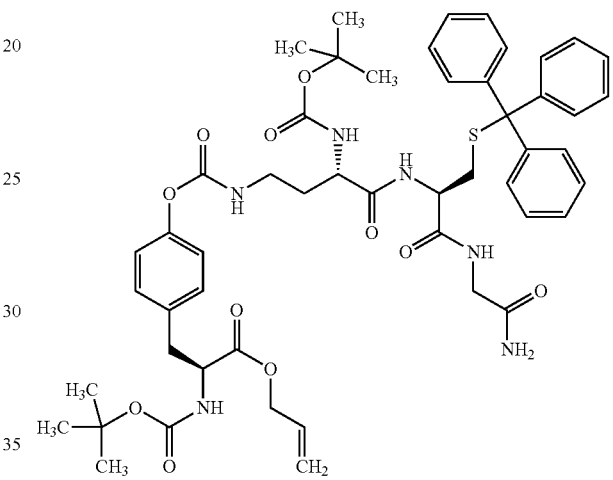

173 mg (0.31 mmol) of the compound from example 2A was dissolved in 10 ml dichloromethane. 128 mg (0.31 mmol) S-Trityl-L-cysteinylglycinamide, 53 μl (0.31 mmol) N,N-diisopropylethyl-amine and 116 mg (0.31 mmol) HATU were added. The reaction mixture was heated for 30 min in a sealed tube at 60° C. in a microwave synthesizer. From the reaction mixture the solvent was removed under reduced pressure. The raw product was purified by preparative RP-HPLC on a C18 column with a water methanol gradient from 9/1 to 1/9. The product-containing fractions were combined and concentrated to dryness under reduced pressure. This gave 57 mg (0.02 mmol, 18% of theory) of the desired product.

LC-MS (method 1): $R_t$=1.31 min., m/z=968 (M+H)$^+$

Example 17A

N-[(9H-Fluoren-9-ylmethoxy)carbonyl]glycyl-S-trityl-L-cysteinamide

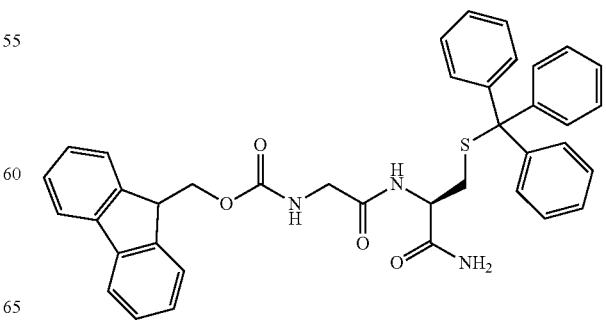

1.00 g (3.36 mmol) of N-[(9H-Fluoren-9-ylmethoxy)carbonyl]glycine was dissolved in 30 ml dichloromethane. 1.41 g (3.36 mmol) S-Trityl-L-cysteinylglycinamide, 0.59 ml (3.36 mmol) N,N-diisopropylethylamine and 1.28 g (3.36 mmol) HATU were added. The reaction mixture was heated for 30 min in a sealed tube at 60° C. in a microwave synthesizer. From the reaction mixture the solvent was removed under reduced pressure. The raw product was dissolved in dichloromethane and chromatographed over approx. 300 ml silica gel. Solvents used were dichloromethane, dichloromethane/methanol 20/1, dichloromethane/methanol 10/1. The product-containing fractions were combined and concentrated to dryness under reduced pressure. This gave 1.63 g (2.06 mmol, 81% of theory) of the desired product.

LC-MS (method 1): $R_t$=1.31 min., m/z=642 (M+H)$^+$

Example 18A

Glycyl-S-trityl-L-cysteinamide

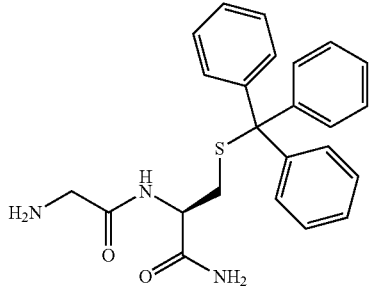 [SMILES: NCC(=O)N[C@@H](CSC(c1ccccc1)(c1ccccc1)c1ccccc1)C(N)=O]

1.53 g (2.38 mmol) of the compound from example 17A was dissolved in 18 ml dimethyl formamide and 0.47 ml (4.79 mmol) DIEA was added. After one hour reaction time, the raw product was purified by preparative RP-HPLC on a C18 column with a water methanol gradient from 9/1 to 1/9. The product-containing fractions were combined and concentrated to dryness under reduced pressure. This gave 416 mg (0.97 mmol, 40% of theory) of the desired product.

LC-MS (method 1): $R_t$=0.76 min., m/z=418 (M–H)$^-$

Example 19A

N-{(2S)-4-{[(4-{(2S)-3-(Allyloxy)-2-[(tert-butoxycarbonyl)amino]-3-oxopropyl}phenoxy)-carbonyl]amino}-2-[(tert-butoxycarbonyl)amino]butanoyl}glycyl-S-trityl-L-cysteinamide

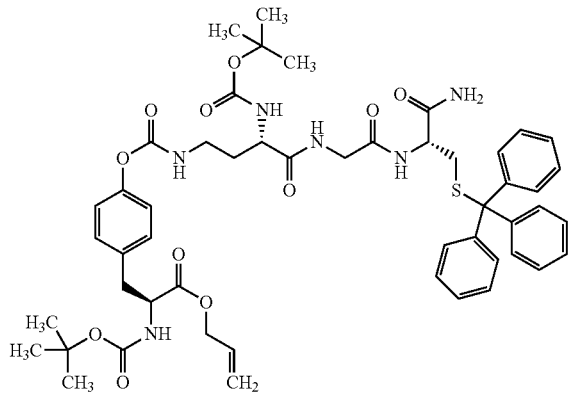 [SMILES: C=CCOC(=O)[C@H](Cc1ccc(OC(=O)NCC[C@H](NC(=O)OC(C)(C)C)C(=O)NCC(=O)N[C@@H](CSC(c2ccccc2)(c2ccccc2)c2ccccc2)C(N)=O)cc1)NC(=O)OC(C)(C)C]

559 mg (0.99 mmol) of the compound from example 2A was dissolved in 15 ml dichloromethane. 415 mg (0.99 mmol) of the compound from example 18A, 173 μl (0.99 mmol) N,N-diisopropylethylamine and 376 mg (0.99 mmol) HATU were added. The reaction mixture was heated for 30 min in a sealed tube at 60° C. in a microwave synthesizer. From the reaction mixture the solvent was removed under reduced pressure. The raw product was dissolved in dichloromethane and chromatographed over approx. 70 ml silica gel. Solvents used were dichloromethane, dichloromethane/methanol 20/1 to dichloromethane/methanol 5/1. The product-containing fractions were combined and concentrated to dryness under reduced pressure. This gave 860 mg (0.69 mmol, 70% of theory) of the desired product.

LC-MS (method 1): $R_t$=1.30 min., m/z=968 (M+H)$^+$

Example 20A

9H-Fluoren-9-ylmethyl-(6-{[(2R)-1-amino-1-oxo-3-(tritylsulfanyl)propan-2-yl]amino}-6-oxohexyl)carbamate

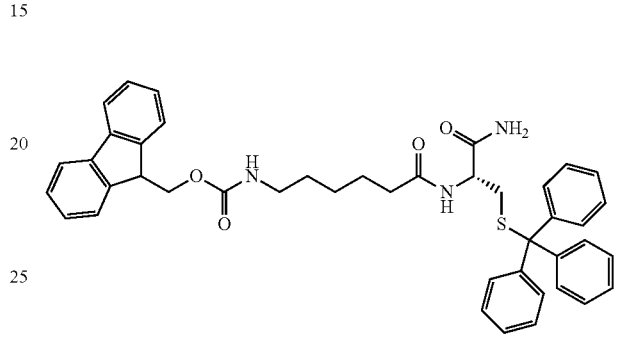

500 mg (1.42 mmol) 6-{[(9H-Fluoren-9-ylmethoxy)carbonyl]amino}hexanoic acid was dissolved in 18 ml dichloromethane. 513 mg (1.42 mmol) S-Trityl-L-cysteinylglycinamide, 246 μl (1.42 mmol) N,N-diisopropylethylamine and 537 m g (1.42 mmol) HATU were added. The reaction mixture was heated for 30 min in a sealed tube at 60° C. in a microwave synthesizer. From the reaction mixture the solvent was removed under reduced pressure. The raw product was purified by preparative RP-HPLC on a C18 column with a water methanol gradient from 9/1 to 1/9. The product-containing fractions were combined and concentrated to dryness under reduced pressure. This gave 678 mg (0.70 mmol, 49% of theory) of the desired product.

LC-MS (method 1): $R_t$=1.38 min., m/z=698 (M+H)$^+$

Example 21A

6-Amino-N-[(2R)-1-amino-1-oxo-3-(tritylsulfanyl)propan-2-yl]hexanamide

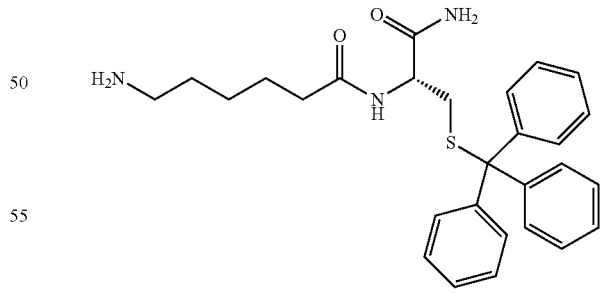

678 mg (0.97 mmol) of the compound of example 20A was dissolved in 7 ml dimethyl formamide and 0.19 ml (1.94 mmol) DIEA was added. After one hour reaction time, the raw product was purified by preparative RP-HPLC on a C18 column with a water methanol gradient from 9/1 to 1/9. The product-containing fractions were combined and concentrated to dryness under reduced pressure. This gave 457 mg (0.93 mmol, 95% of theory) of the desired product.

LC-MS (method 1): $R_t$=0.85 min., m/z=476 (M+H)$^+$

Example 22A

Allyl-O-({(3S)-4-[(6-{[(2R)-1-amino-1-oxo-3-(tritylsulfanyl)propan-2-yl]amino}-6-oxohexyl)-amino]-3-[(tert-butoxycarbonyl)amino]-4-oxobutyl}carbamoyl)-N-(tert-butoxycarbonyl)-L-tyrosinate

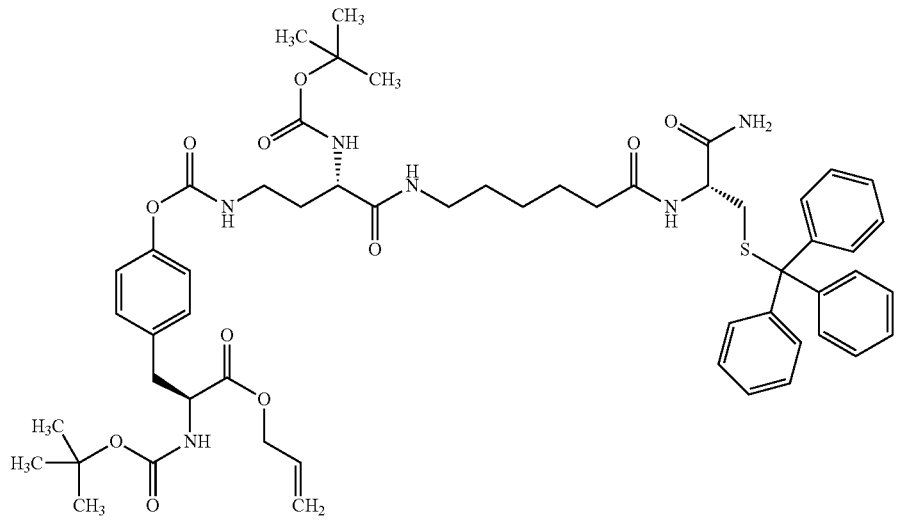 [SMILES: C=CCOC(=O)[C@H](Cc1ccc(OC(=O)NCC[C@H](NC(=O)OC(C)(C)C)C(=O)NCCCCCC(=O)N[C@@H](CSC(c2ccccc2)(c2ccccc2)c2ccccc2)C(N)=O)cc1)NC(=O)OC(C)(C)C]

457 mg (0.81 mmol) of the compound from example 2A was dissolved in 15 ml dichloromethane. 384 mg (0.81 mmol) of the compound from example 21A, 141 µl (0.81 mmol) N,N-diisopropylethylamine and 307 mg (0.81 mmol) HATU were added. The reaction mixture was heated for 30 min in a sealed tube at 60° C. in a microwave synthesizer. From the reaction mixture the solvent was removed under reduced pressure. The raw product was purified in two portions by preparative RP-HPLC on a C18 column with a water methanol gradient from 9/1 to 1/9. The product-containing fractions were combined and concentrated to dryness under reduced pressure. This gave 255 mg (0.22 mmol, 28% of theory) of the desired product.

LC-MS (method 1): $R_t$=1.31 min., m/z=1032 (M+H)$^+$

Example 23A

Allyl-O-({(14S)-1-azido-14-[(tert-butoxycarbonyl)amino]-13-oxo-3,6,9-trioxa-12-azahexadecan-16-yl}carbamoyl)-N-(tert-butoxycarbonyl)-L-tyrosinate

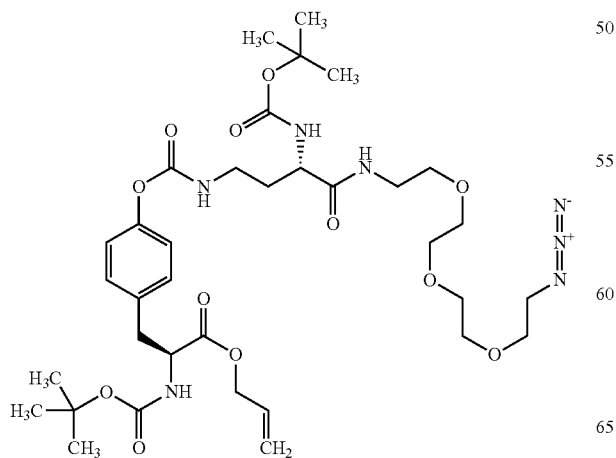

518 mg (0.92 mmol) of the compound from example 2A was dissolved in 15 ml dichloromethane. 200 mg (0.92 mmol) 2-{2-[2-(2-Azidoethoxy)ethoxy]ethoxy}ethanamine, 160 µl (0.92 mmol) N,N-diisopropylethylamine and 348 mg (0.92 mmol) HATU were added. The reaction mixture was heated for 30 min in a sealed tube at 60° C. in a microwave synthesizer. From the reaction mixture the solvent was removed under reduced pressure. The raw product was purified by preparative RP-HPLC on a C18 column with a water methanol gradient from 9/1 to 1/9. The product-containing fractions were combined and concentrated to dryness under reduced pressure. This gave 276 mg (0.34 mmol, 37% of theory) of the desired product.

LC-MS (method 1): $R_t$=1.15 min., m/z=766 (M+H)$^+$

Example 24A

N-[(4-{(2S)-3-(Allyloxy)-2-[(tert-butoxycarbonyl)amino]-3-oxopropyl}phenoxy)carbonyl]-3-[(tert-butoxycarbonyl)amino]-L-alanine

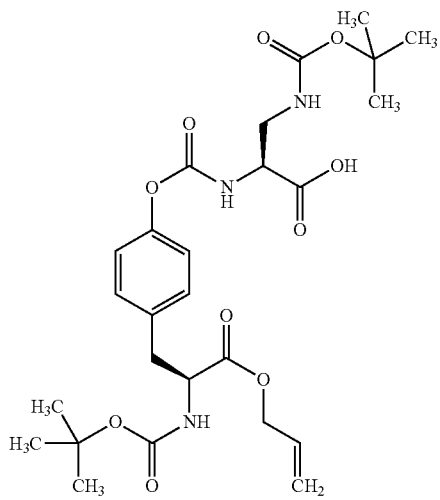 [SMILES: C=CCOC(=O)[C@H](Cc1ccc(OC(=O)N[C@@H](CNC(=O)OC(C)(C)C)C(=O)O)cc1)NC(=O)OC(C)(C)C]

2.45 g (5.0 mmol) of the compound from example 1A was dissolved in 40 ml dichloroethane. 1.03 g, (5.0 mmol) 3-[(tert-Butoxycarbonyl)amino]-L-alanine was added. The reaction mixture was heated to 85° C. for 2 h. The solvent was removed under reduced pressure. The raw product was dissolved in dichloromethane and chromatographed over approx. 150 ml silica gel. Solvents used were dicloromethane/methanol 20/1 to dichloromethane/methanol 1/1. The product-containing fractions were combined and concentrated to dryness under reduced pressure. This gave 1.23 g (2.2 mmol, 44% of theory) of the desired product.

LC-MS (method 1): $R_t$=1.06 min., m/z=550 (M–H)⁻

Example 25A

N-[(4-{(2S)-3-(Allyloxy)-2-[(tert-butoxycarbonyl)amino]-3-oxopropyl}phenoxy)carbonyl]-3-[(tert-butoxycarbonyl)amino]-L-alanyl-S-trityl-L-cysteinamide

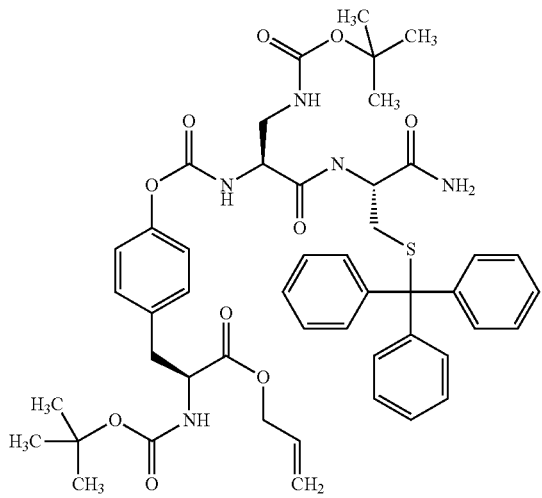 [SMILES: C=CCOC(=O)[C@H](Cc1ccc(OC(=O)N[C@@H](CNC(=O)OC(C)(C)C)C(=O)N[C@@H](CSC(c2ccccc2)(c2ccccc2)c2ccccc2)C(N)=O)cc1)NC(=O)OC(C)(C)C]

1.23 g (2.23 mmol) of the compound from example 24A was dissolved in 25 ml dichloromethane. 0.81 g (2.23 mmol) S-Trityl-L-cysteinamide, 0.39 ml (2.23 mmol) N,N-diisopropylethylamine and 0.85 g (2.23 mmol) HATU were added. The reaction mixture was stirred at room temperature for 3 h. From the reaction mixture the solvent was removed by rotary evaporation (approx. 40° C., approx. 200 mbar, approx. 30 min.). The raw product was dissolved in dichloromethane and chromatographed over approx. 70 ml silica gel. Solvents used were dichloromethane/methanol 20/1 to dichloromethane/methanol 5/1. The product-containing fractions were combined and concentrated to dryness under reduced pressure. This gave 2.38 g (2.03 mmol, 91% of theory, 76% purity) of the desired product.

LC-MS (method 1): $R_t$=1.37 min., m/z=897 (M+H)⁺

Example 26A

Allyl-O-({(3S)-4-{[(2R)-1-anilino-1-oxo-3-(tritylsulfanyl)propan-2-yl]amino}-3-[(tert-butoxycarbonyl)amino]-4-oxobutyl}carbamoyl)-N-(tert-butoxycarbonyl)-L-tyrosinate

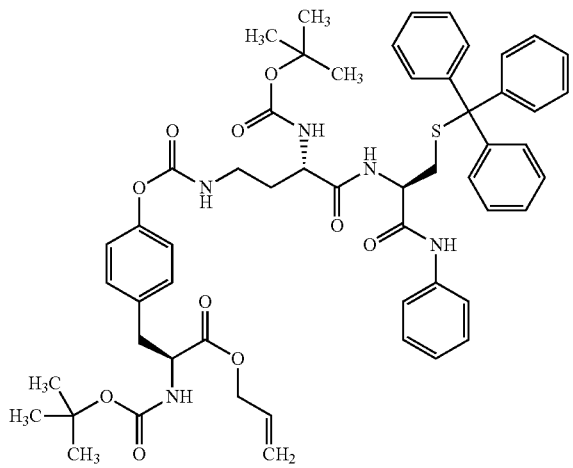 [SMILES: C=CCOC(=O)[C@H](Cc1ccc(OC(=O)NCC[C@H](NC(=O)OC(C)(C)C)C(=O)N[C@@H](CSC(c2ccccc2)(c2ccccc2)c2ccccc2)C(=O)Nc2ccccc2)cc1)NC(=O)OC(C)(C)C]

456 mg (0.68 mmol) of the compound from example 2A was dissolved in 8 ml dichloromethane. 300 mg (0.68 mmol) N-Phenyl-S-trityl-L-cysteinamide, 0.12 ml (0.68 mmol) N,N-diisopropylethylamine and 260 mg (0.68 mmol) HATU were added. The reaction mixture was stirred at room temperature for 4 h. From the reaction mixture the solvent was removed under reduced pressure. The raw product was purified in two portions by preparative RP-HPLC on a C18 column with a water methanol gradient from 9/1 to 1/9. The product-containing fractions were combined and concentrated to dryness under reduced pressure. This gave 361 mg (0.37 mmol, 53% of theory) of the desired product.

LC-MS (method 1): $R_t$=1.48 min., m/z=987 (M+H)⁺

Example 1B tert-Butyl-[(2S)-1-{[(2R)-1-amino-1-oxo-3-(tritylsulfanyl)propan-2-yl]amino}-4-{[(4-{(2S)-3-anilino-2-[(tert-butoxycarbonyl)amino]-3-oxopropyl}phenoxy)carbonyl]amino}-1-oxobutan-2-yl]carbamate

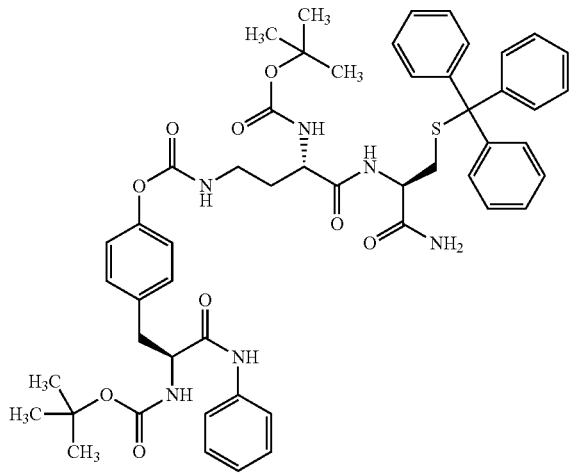 [SMILES: CC(C)(C)OC(=O)N[C@@H](Cc1ccc(OC(=O)NCC[C@H](NC(=O)OC(C)(C)C)C(=O)N[C@@H](CSC(c2ccccc2)(c2ccccc2)c2ccccc2)C(N)=O)cc1)C(=O)Nc1ccccc1]

250 mg (0.29 mmol) of the compound of example 1 was dissolved in 10 ml dichloromethane. 40 mg (0.43 mmol) Aniline, 164 mg (0.43 mmol) HATU and 75 µl (0.43 mmol) DIEA were added. The reaction mixture was heated for 30 min in a sealed tube at 60° C. in a microwave synthesizer. The raw product was concentrated to dryness under reduced pressure. The raw product was dissolved in methanol and purified by preparative RP-HPLC on a C18 column with a water/methanol gradient to yield 271 mg product (88% of theory).

LC-MS (method 1): $R_t$=1.31 min., m/z=945 (M+H)$^+$

Using the appropriate carboxylic acids (working examples 2 to 12), the examples of the table below are prepared analogously to Example 1B.

| Example | Structure | Characterization |
|---|---|---|
| 2B | 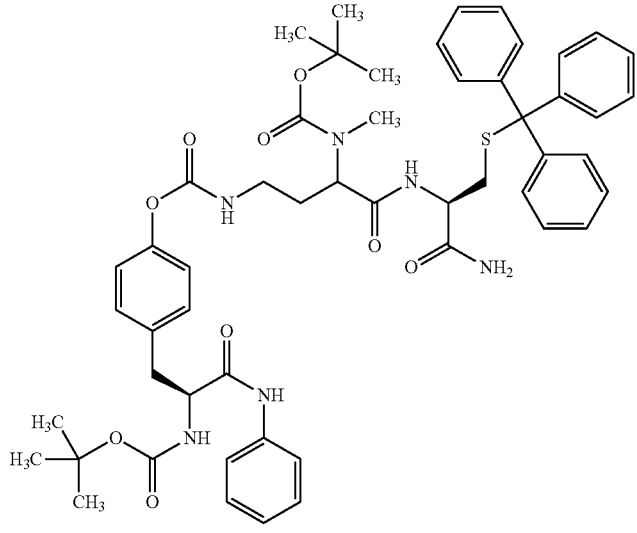 [SMILES: CN(C(=O)OC(C)(C)C)C(CCNC(=O)Oc1ccc(C[C@H](NC(=O)OC(C)(C)C)C(=O)Nc2ccccc2)cc1)C(=O)N[C@@H](CSC(c1ccccc1)(c1ccccc1)c1ccccc1)C(N)=O] | LC-MS (method 1): $R_t$ = 1.34 and 1.37 min., m/z = 959 (M + H)$^+$ |
| 3B | 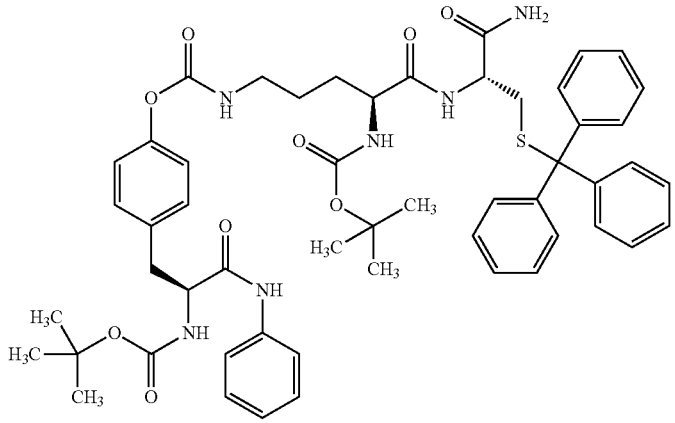 [SMILES: CC(C)(C)OC(=O)N[C@@H](Cc1ccc(OC(=O)NCCC[C@H](NC(=O)OC(C)(C)C)C(=O)N[C@@H](CSC(c2ccccc2)(c2ccccc2)c2ccccc2)C(N)=O)cc1)C(=O)Nc1ccccc1] | LC-MS (method 1): $R_t$ = 1.32 min., m/z = 959 (M + H)$^+$ |

-continued
| Example | Structure | Characterization |
|---|---|---|
| 4B | 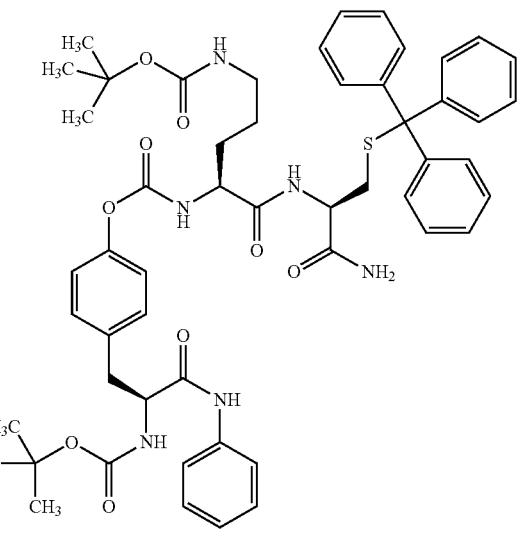 | LC-MS (method 1):<br>$R_t$ = 1.32 min.,<br>m/z = 959 (M + H)$^+$ |
| 5B | 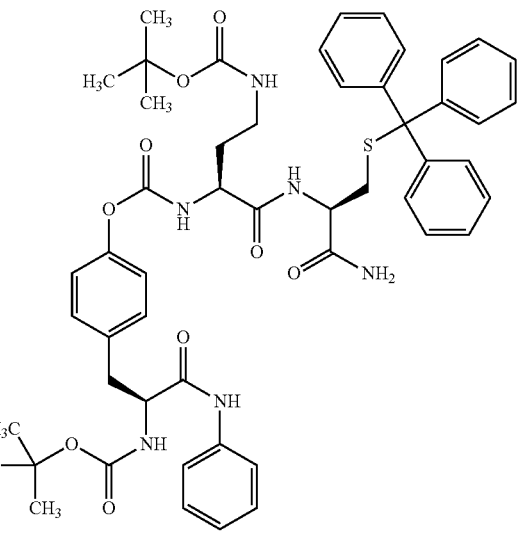 | LC-MS (method 1):<br>$R_t$ = 1.30 min,<br>m/z = 945 (M + H)$^+$ |
| 6B | 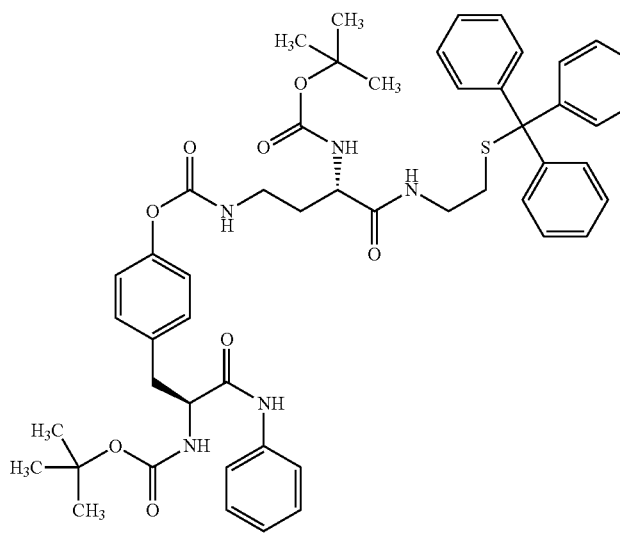 | LC-MS (method 1):<br>$R_t$ = 1.43 min,<br>m/z = 903 (M + H)$^+$ |

-continued
| Example | Structure | Characterization |
|---------|-----------|------------------|
| 7B | 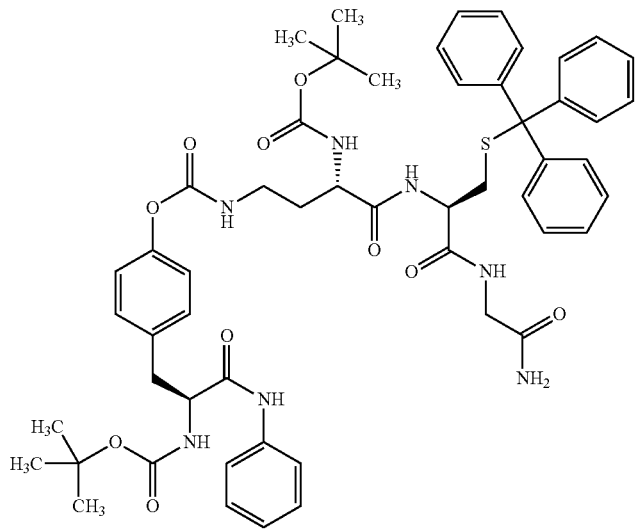 [SMILES: CC(C)(C)OC(=O)N[C@@H](Cc1ccc(OC(=O)NCC[C@H](NC(=O)OC(C)(C)C)C(=O)N[C@@H](CSC(c2ccccc2)(c2ccccc2)c2ccccc2)C(=O)NCC(N)=O)cc1)C(=O)Nc1ccccc1] | LC-MS (method 1): $R_t$ = 1.29 min, m/z = 1002 (M + H)$^+$ |
| 8B | 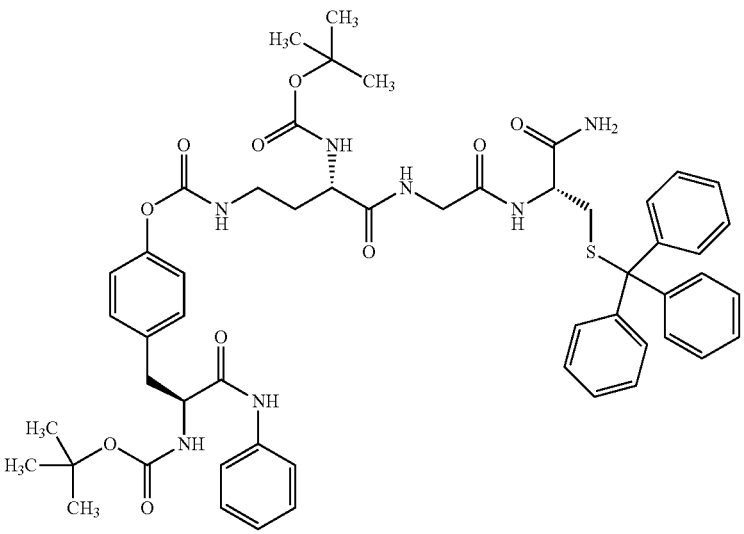 [SMILES: CC(C)(C)OC(=O)N[C@@H](CCNC(=O)Oc1ccc(C[C@H](NC(=O)OC(C)(C)C)C(=O)Nc2ccccc2)cc1)C(=O)NCC(=O)N[C@@H](CSC(c1ccccc1)(c1ccccc1)c1ccccc1)C(N)=O] | LC-MS (method 1): $R_t$ = 1.27 min, m/z = 1002 (M + H)$^+$ |
| 9B | 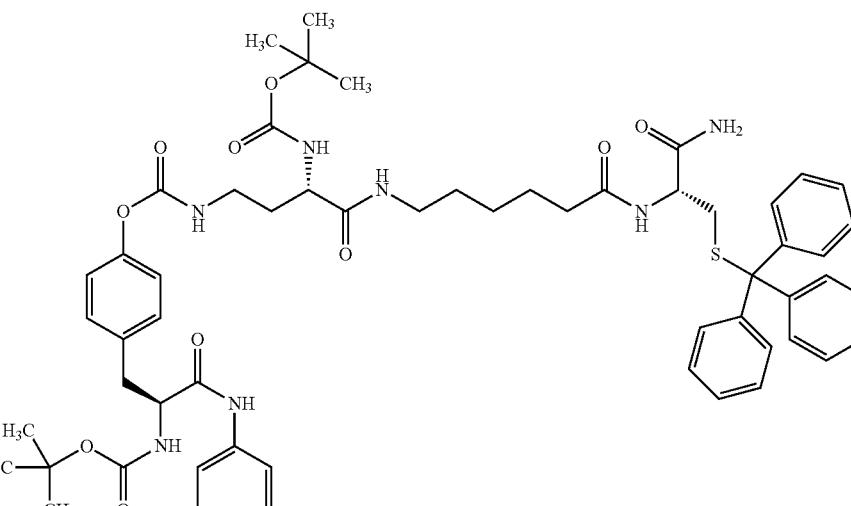 | LC-MS (method 1): $R_t$ = 1.29 min, m/z = 1058 (M + H)$^+$ |

-continued
| Example | Structure | Characterization |
|---------|-----------|------------------|
| 10B | 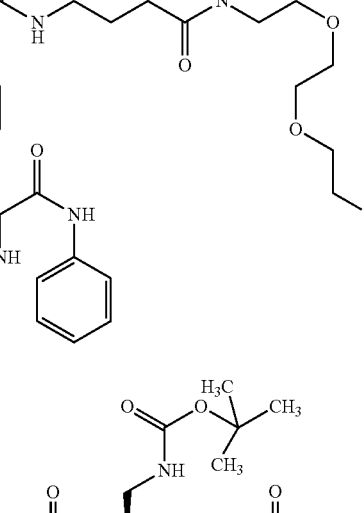 | LC-MS (method 2):<br>$R_t$ = 2.42 min,<br>m/z = 801 (M + H)$^+$ |
| 11B | 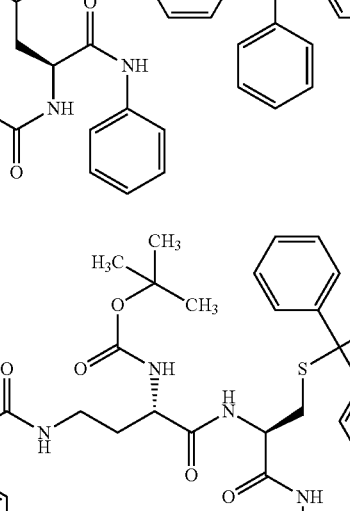 | LC-MS (method 1):<br>$R_t$ = 1.36 min,<br>m/z = 931 (M + H)$^+$ |
| 12B | 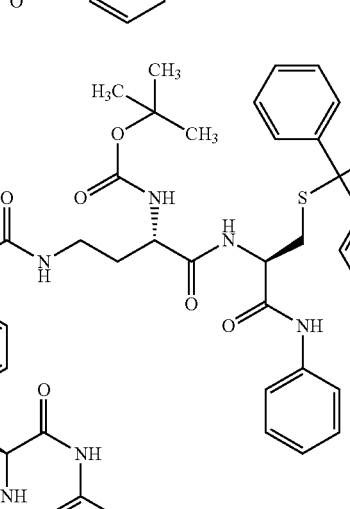 | LC-MS (method 1):<br>$R_t$ = 1.48 min,<br>m/z = 1022 (M + H)$^+$ |

Example 1C

O-{[(3S)-3-Amino-4-({(2R)-1-amino-3-[(1-benzyl-2,5-dioxopyrrolidin-3-yl)sulfanyl]-1-oxopropan-2-yl}amino)-4-oxobutyl]carbamoyl}-N-phenyl-L-tyrosinamide

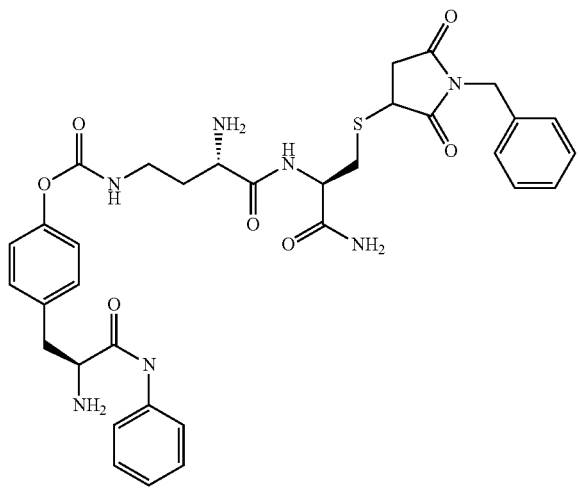 [SMILES: NC(=O)[C@H](CSC1CC(=O)N(Cc2ccccc2)C1=O)NC(=O)[C@@H](N)CCNC(=O)Oc1ccc(C[C@H](N)C(=O)Nc2ccccc2)cc1]

238 mg (0.25 mmol) of the compound of example 1B was dissolved in 10 ml dichloroethane. 0.12 ml Triethylsilane, approx. 10 ml trifluoroacetic acid and approx. 0.5 ml water was added. The reaction mixture was stirred for approx. 30 min at room temperature. 100 ml dichloroethane were added and the reaction mixture was evaporated under reduced pressure to approx. 1 ml of solvent volume. Approx. 100 ml water was added and the reaction mixture was extracted three times with approx. 50 ml dichloromethane. To the aqueous phase 15 ml of acetic acid was added. The aqueous phase was frozen and lyophilized. The lyophylistae was dissolved in approx. 50 ml methanol and 0.183 mg (0.98 mmol) N-benzylmaleimide was added. The reaction mixture was stirred over night at room temperature. The reaction mixture was evaporated to dryness and redissolved in approx. 5 ml methanol and purified by preparative RP-HPLC on a C18 with a water/methanol gradient. The fractions were collected in test tubes of 20 ml on an automated fraction collector. To ensure sufficient acidity each vial was filled with 0.5 ml acedic acid prior to collection. All fractions containing the compound of example 1C were combined. Acetonitrile was partially removed on a rotary evaporator at 30° C. water bath temperature and approx. 50 mbar for approx. 30 min. After addition of 0.5 ml acedic acid, the remaining solution was lyophilized. The total yield was 168 mg (0.24 mmol, 98% of theory) of the desired product.

LC-MS (method 1): $R_t$=0.55 min., m/z=690 (M+H)$^+$

Using the appropriate precursors (examples 2B to 9B), the examples of the table below are prepared analogously to example 1C.

| Example | Structure | Characterization |
|---|---|---|
| 2C | (structure shown) | LC-MS (method 1): $R_t$ = 0.64 min., m/z = 704 (M + H)$^+$ |

-continued

| Example | Structure | Characterization |
|---|---|---|
| 3C | 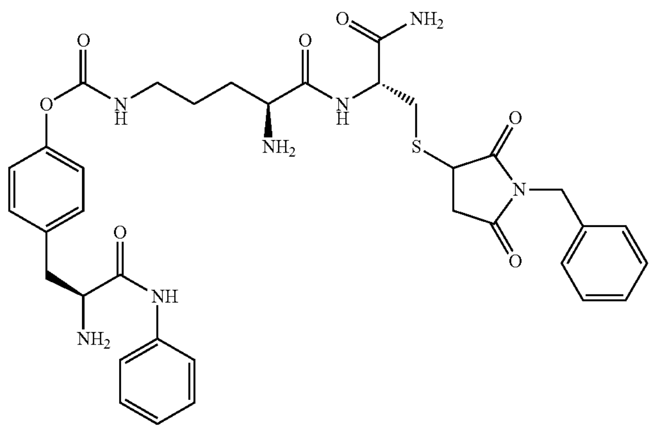 [SMILES: NC(=O)[C@H](CSC1CC(=O)N(Cc2ccccc2)C1=O)NC(=O)[C@@H](N)CCCNC(=O)Oc1ccc(C[C@H](N)C(=O)Nc2ccccc2)cc1] | LC-MS (method 1): $R_t$ = 0.63 min., m/z = 704 (M + H)$^+$ |
| 4C | 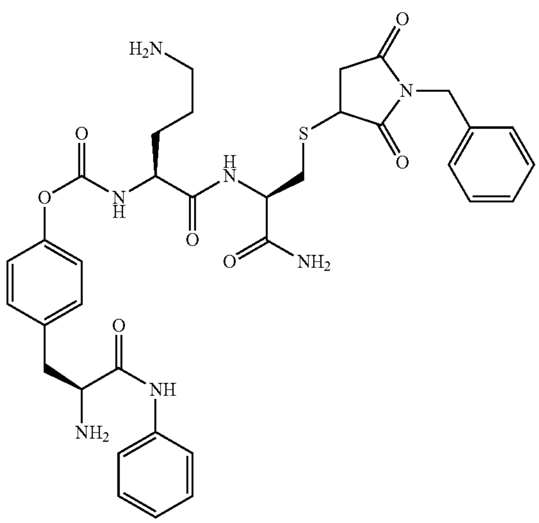 [SMILES: NCCC[C@H](NC(=O)Oc1ccc(C[C@H](N)C(=O)Nc2ccccc2)cc1)C(=O)N[C@@H](CSC1CC(=O)N(Cc2ccccc2)C1=O)C(N)=O] | LC-MS (method 1): $R_t$ = 0.61 min., m/z = 704 (M + H)$^+$ |
| 5C | 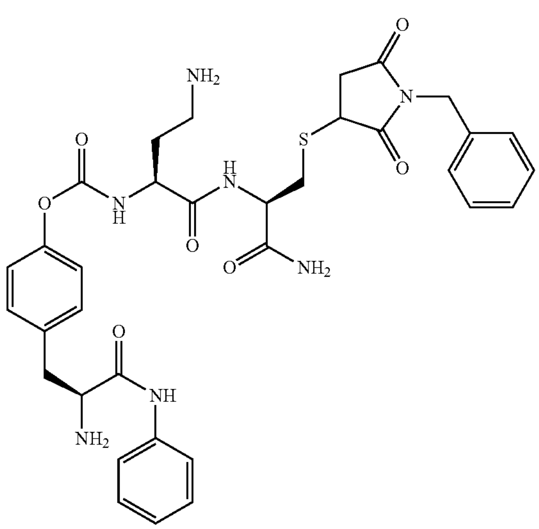 [SMILES: NCC[C@H](NC(=O)Oc1ccc(C[C@H](N)C(=O)Nc2ccccc2)cc1)C(=O)N[C@@H](CSC1CC(=O)N(Cc2ccccc2)C1=O)C(N)=O] | LC-MS (method 1): $R_t$ = 0.55 min., m/z = 690 (M + H)$^+$ |

| Example | Structure | Characterization |
|---|---|---|
| 6C | 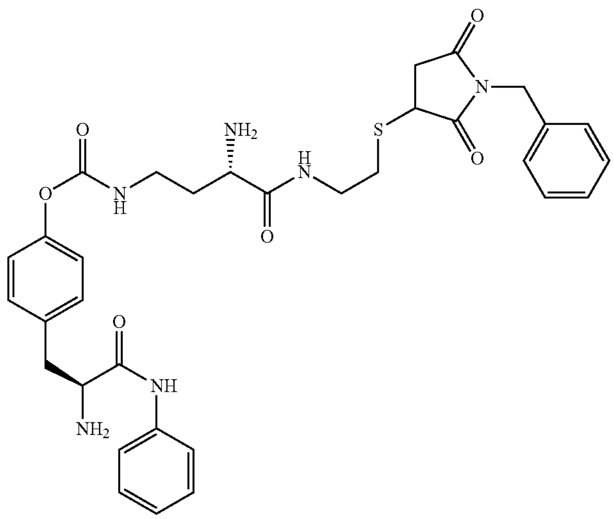 [SMILES: N[C@@H](CCNC(=O)Oc1ccc(C[C@H](N)C(=O)Nc2ccccc2)cc1)C(=O)NCCSC1CC(=O)N(Cc2ccccc2)C1=O] | LC-MS (method 1): $R_t$ = 0.67 min., m/z = 647 (M + H)$^+$ |
| 7C | 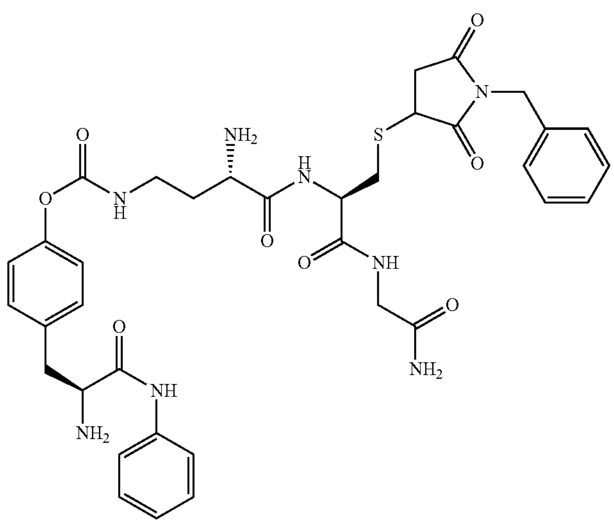 [SMILES: NC(=O)CNC(=O)[C@H](CSC1CC(=O)N(Cc2ccccc2)C1=O)NC(=O)[C@@H](N)CCNC(=O)Oc1ccc(C[C@H](N)C(=O)Nc2ccccc2)cc1] | LC-MS (method 1): $R_t$ = 0.61 min., m/z = 747 (M + H)$^+$ |
| 8C | 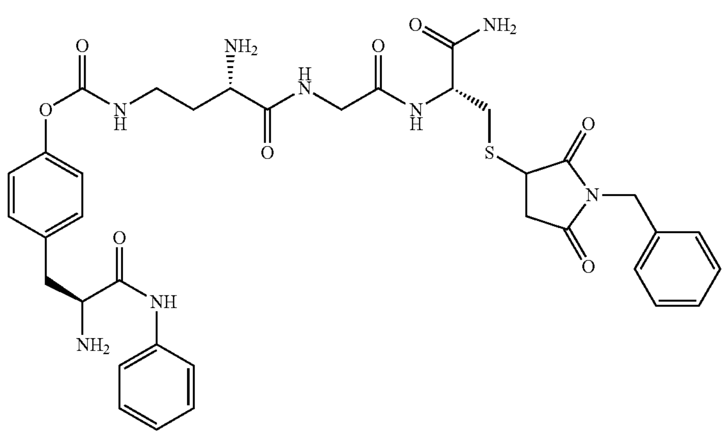 [SMILES: NC(=O)[C@H](CSC1CC(=O)N(Cc2ccccc2)C1=O)NC(=O)CNC(=O)[C@@H](N)CCNC(=O)Oc1ccc(C[C@H](N)C(=O)Nc2ccccc2)cc1] | LC-MS (method 1): $R_t$ = 0.61 min., m/z = 747 (M + H)$^+$ |

| Example | Structure | Characterization |
|---|---|---|
| 9C | 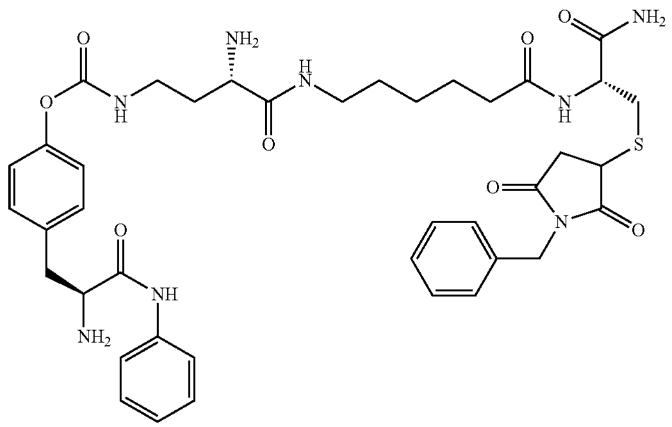 [SMILES: NC(=O)[C@H](CSC1CC(=O)N(Cc2ccccc2)C1=O)NC(=O)CCCCCNC(=O)[C@@H](N)CCNC(=O)Oc1ccc(C[C@H](N)C(=O)Nc2ccccc2)cc1] | LC-MS (method 2): $R_t$ = 1.53 min., m/z = 803 (M + H)$^+$ |

Example 10Ca

Nalpha-(tert-butoxycarbonyl)-O-{[(14S)-14-[(tert-butoxycarbonyl)amino]-13-oxo-1-(4-phenyl-1H-1,2,3-triazol-1-yl)-3,6,9-trioxa-12-azahexadecan-16-yl]carbamoyl}-N-phenyl-L-tyrosinamide

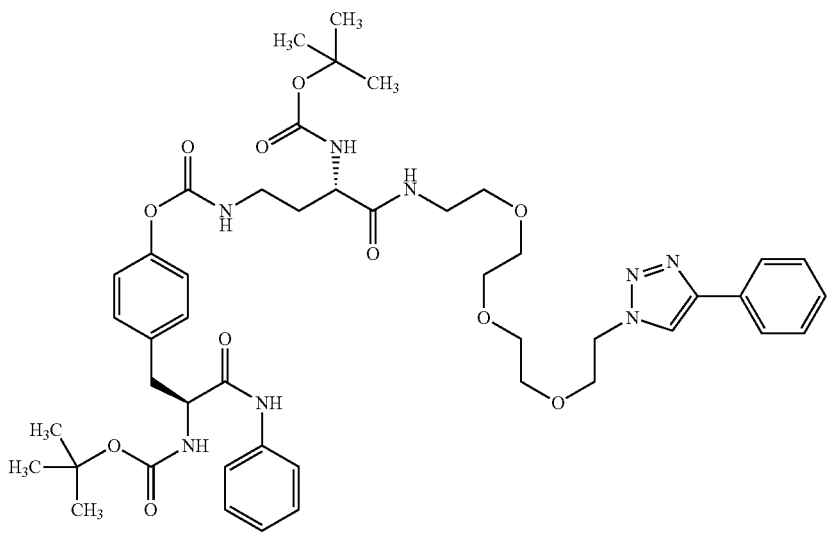 [SMILES: CC(C)(C)OC(=O)N[C@@H](CCNC(=O)Oc1ccc(C[C@H](NC(=O)OC(C)(C)C)C(=O)Nc2ccccc2)cc1)C(=O)NCCOCCOCCOCCn1cc(-c2ccccc2)nn1]

40 mg (0.05 mmol) of the compound of example 10B was dissolved in a mixture of 4 ml DMSO and 1 ml water. 10 mg (0.10 mmol) Phenylacetylene, 0.8 mg copper(II)sulfate (0.005 mmol), 445 mg (2.25 mmol) sodium ascorbate and 1.8 mg (0.01 mmol) 1,10-phenantroline were added. The pH of the reaction mixture was adjusted to 4 by addition of 3 to 4 drops of 10% sulfuric acid and the reaction mixture was stirred over night. The reaction mixture was diluted with approx. 10 ml water and extracted twice with approx. 10 ml ethyl acetate. The combined organic phases were evaporated to dryness and redissolved in approx. 5 ml methanol and purified by preparative RP-HPLC on a C18 with a water/methanol gradient. The product-containing fractions were combined and concentrated to dryness under reduced pressure. This gave 36 mg (0.04 mmol, 79% of theory) of the desired product.

LC-MS (method 1): $R_t$=1.12 min., m/z=903 (M+H)$^+$

Example 10Cb

O-{[(14S)-14-Amino-13-oxo-1-(4-phenyl-1H-1,2,3-triazol-1-yl)-3,6,9-trioxa-12-azahexadecan-16-yl]carbamoyl}-N-phenyl-L-tyrosinamide

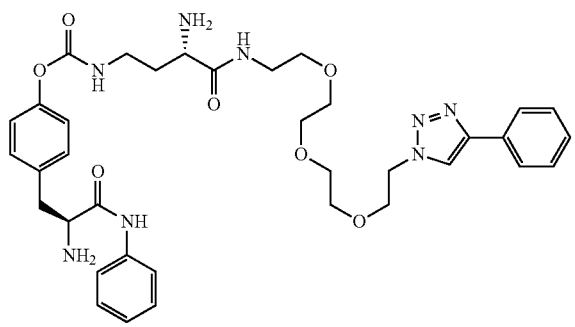 [SMILES: N[C@@H](CCNC(=O)Oc1ccc(C[C@H](N)C(=O)Nc2ccccc2)cc1)C(=O)NCCOCCOCCOCCn1cc(-c2ccccc2)nn1]

36 mg (0.04 mmol) of the compound of example 10Ca was dissolved in 2.5 ml dichloroethane. 0.02 ml Triethylsilane, approx. 2.5 ml trifluoroacetic acid and approx. 0.1 ml water was added. The reaction mixture was stirred for approx. 30 min at room temperature. The reaction mixture was evaporated to dryness, and redissolved in approx. 15 ml water. The reaction mixture was extracted three times with approx. 10 ml of dichloromethane. After addition of approx. 0.5 ml acetic acid, the aqueous phase was lyophilized. The lyophylisate was redissolved in approx. 5 ml methanol and purified by preparative RP-HPLC on a C18 with a water/methanol gradient. The product-containing fractions were combined and concentrated to dryness under reduced pressure. This gave 13 mg (0.02 mmol, 45% of theory) of the desired product.

LC-MS (method 1): $R_t$=0.57 min., m/z=703 (M+H)$^+$

Using the appropriate precursors (examples 11B and 12B), the examples of the table below are prepared analogously to example 1C.

| Example | Structure | Characterization |
|---|---|---|
| 11C | 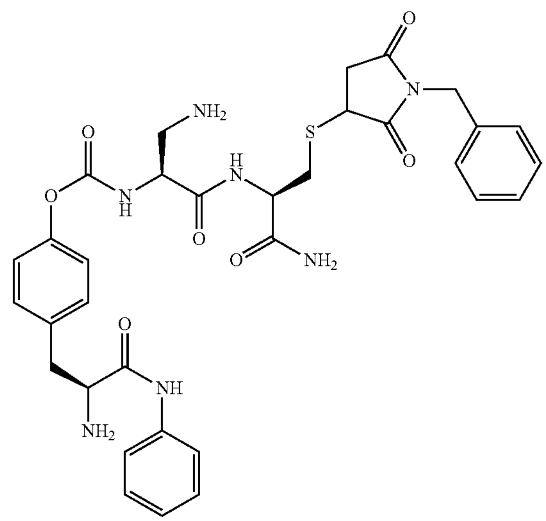 [SMILES: NC[C@H](NC(=O)Oc1ccc(C[C@H](N)C(=O)Nc2ccccc2)cc1)C(=O)N[C@@H](CSC1CC(=O)N(Cc2ccccc2)C1=O)C(N)=O] | LC-MS (method 1): $R_t$ = 0.60 min., m/z = 676 (M + H)$^+$ |
| 12C | 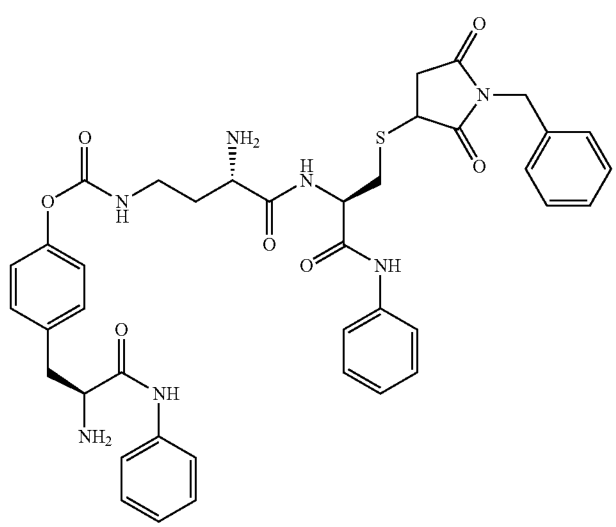 [SMILES: N[C@@H](Cc1ccc(OC(=O)NCC[C@H](N)C(=O)N[C@@H](CSC2CC(=O)N(Cc3ccccc3)C2=O)C(=O)Nc2ccccc2)cc1)C(=O)Nc1ccccc1] | LC-MS (method 2): $R_t$ = 1.69 min., m/z = 767 (M + H)$^+$ |

WORKING EXAMPLES

Example 1

O-({(3S)-4-{[(2R)-1-Amino-1-oxo-3-(tritylsulfanyl)propan-2-yl]amino}-3-[(tert-butoxycarbonyl)-amino]-4-oxobutyl}carbamoyl)-N-(tert-butoxycarbonyl)-L-tyrosine

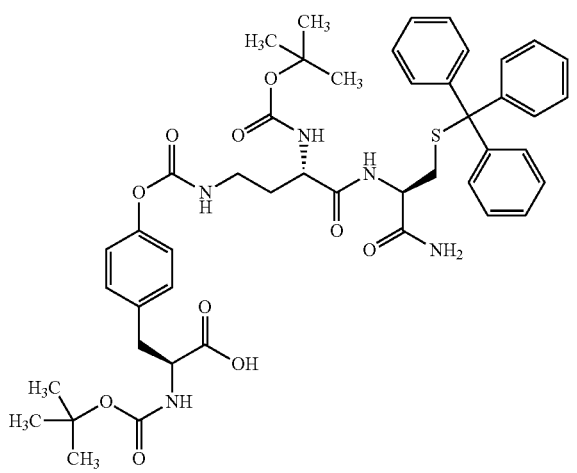 [SMILES: CC(C)(C)OC(=O)N[C@@H](Cc1ccc(OC(=O)NCC[C@H](NC(=O)OC(C)(C)C)C(=O)N[C@@H](CSC(c2ccccc2)(c2ccccc2)c2ccccc2)C(N)=O)cc1)C(=O)O]

4.14 g (4.55 mmol) of the compound from example 3A was dissolved in 90 ml tetrahydrofuran. 3.17 ml (22.8 mmol) triethylamine, 0.86 ml (22.8 mmol) formic acid and 0.526 g (0.455 mmol) tetrakis(triphenylphosphin)palladium(0) were added. The reaction mixture was stirred over night at room temperature. The reaction was diluted with approx. 100 ml water, and twice extracted with approx. 100 ml dichloromethane. The combined organic phases were extracted with brine, dried over sodium sulfate and concentrated to dryness under reduced pressure. The raw product was dissolved in dichloromethane and chromatographed over approx. 500 ml silica gel. Solvents used were dichloromethane, dichloromethane/methanol 20/1 and dichloromethane/methanol 1/1. The product-containing fractions were combined and concentrated to dryness under reduced pressure. This gave 2.62 g raw product of 94.5% purity. The product was further purified by preparative RP-HPLC on a C18 with a water/methanol gradient to yield 2.35 g (2.70 mmol, 59% of theory) pure product.

LC-MS (method 1): $R_t$=1.22 min., m/z=871 (M+H)$^+$ $^1$H-NMR (400 MHz, DMSO-d$_6$, δ/ppm): δ=7.92 (d, 1H), 7.65 (t, 1H), 7.28-7.35 (m, 12H), 7.25-7.28 (t, 3H), 7.15-7.20 (m, 4H), 6.95 (d, 2H), 4.29 (q, 1H), 4.00 (m, 1H), 3.92 (m, 1H), 3.11 (m, 3H), 2.90 (m, 1H), 2.36 (m, 2H), 1.84 (m, 1H), 1.68 (m, 1H), 1.34 (d, 18H).

Example 2

O-[(4-{[(2R)-1-Amino-1-oxo-3-(tritylsulfanyl)propan-2-yl]amino}-3-[(tert-butoxycarbonyl)-(methyl)amino]-4-oxobutyl)carbamoyl]-N-(tert-butoxycarbonyl)-L-tyrosine

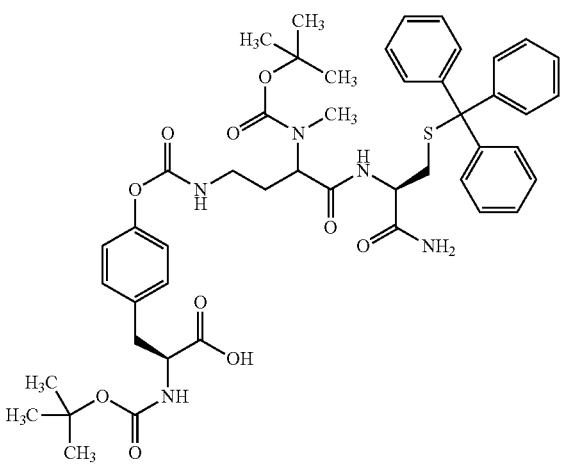 [SMILES: CN(C(=O)OC(C)(C)C)C(CCNC(=O)Oc1ccc(C[C@H](NC(=O)OC(C)(C)C)C(=O)O)cc1)C(=O)N[C@@H](CSC(c1ccccc1)(c1ccccc1)c1ccccc1)C(N)=O]

2.2 g (2.38 mmol) of the compound from example 8A was dissolved in 48 ml tetrahydrofuran. 1.66 ml (11.9 mmol) triethylamine, 0.45 ml (11.9 mmol) formic acid and 0.275 g (0.238 mmol) tetrakis(triphenylphosphin)palladium(0) were added. The reaction mixture was stirred over night at room temperature. The reaction was diluted with approx. 50 ml water and twice extracted with approx. 50 ml dichloromethane. The combined organic phases were extracted with brine, dried over sodium sulfate and concentrated to dryness under reduced pressure. The raw product was dissolved in dichloromethane and chromatographed over approx. 100 g silica gel. Solvents used were dichloromethane, dichloromethane/methanol 50/1 and dichloromethane/methanol 4/1. The product-containing fractions were combined and concentrated to dryness under reduced pressure. This gave 1.44 g (1.61 mmol, 68% of theory) product as a mixture of diastereomers.

LC-MS (method 1): $R_t$=1.20 and 1.24 min., m/z=884 (M+H)$^+$ $^1$H-NMR (400 MHz, DMSO-d$_6$, δ/ppm): δ=8.00 (m, 1H), 7.65-7.90 (m, 4H), 7.18-7.35 (m, 18H), 7.10 (m, 2H), 6.96 (m, 4H), 4.60 (m, 1H), 4.46 (m, 1H), 4.30 (m, 2H), 4.05 (m, 2H), 3.00 (m, 4H), 2.75 (m, 6H), 2.36 (m, 3H), 2.00 (m, 2H), 1.82 (m, 2H), 1.40 (m, 3H), 1.35 (s, 18H).

Example 3

N$^2$-(tert-Butoxycarbonyl)-N$^5$-[(4-{(2S)-2-[(tert-butoxycarbonyl)amino]-2-carboxyethyl}phenoxy)-carbonyl]-L-ornithyl-S-trityl-L-cysteinamide

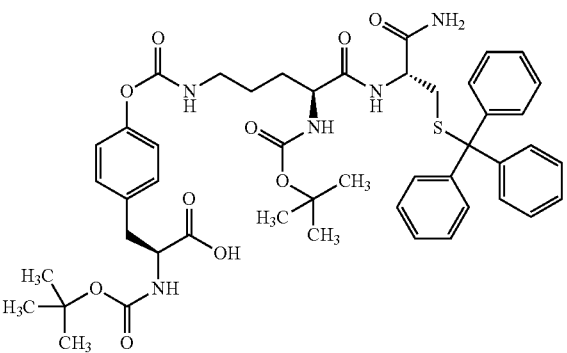 [SMILES: CC(C)(C)OC(=O)N[C@@H](Cc1ccc(OC(=O)NCCC[C@H](NC(=O)OC(C)(C)C)C(=O)N[C@@H](CSC(c2ccccc2)(c2ccccc2)c2ccccc2)C(N)=O)cc1)C(=O)O]

3.06 g (2.33 mmol) of the compound from example 10A was dissolved in 46 ml tetrahydrofuran. 1.63 ml (11.6 mmol) triethylamine, 0.44 ml (11.6 mmol) formic acid and 0.265 g (0.233 mmol) tetrakis(triphenylphosphin)palladium(0) were added. The reaction mixture was stirred over night at room temperature. The reaction was diluted with approx. 50 ml water and twice extracted with approx. 50 ml dichloromethane. The combined organic phases were extracted with brine, dried over sodium sulfate and concentrated to dryness under reduced pressure. The raw product was dissolved in dichloromethane and chromatographed over approx. 500 ml silica gel. Solvents used were dichloromethane, dichloromethane/methanol 40/1 and dichloromethane/methanol 1/1. The product-containing fractions were combined and concentrated to dryness under reduced pressure. This gave 1.40 g raw product of 86% purity. The product was further purified by preparative RP-HPLC on a C18 column with a water/methanol gradient to yield 2 fractions: 0.93 g product (45% of theory).

LC-MS (method 1): $R_t$=1.18 min., m/z=885 (M+H)$^+$ $^1$H-NMR (400 MHz, DMSO-d$_6$, δ/ppm): δ=7.89 (d, 1H), 7.65 (t, 1H), 7.25-7.35 (m, 12H), 7.20-7.25 (m, 6H), 7.10-7.20 (m, 3H), 6.95 (d, 2H), 4.29 (m, 1H), 4.05 (m, 1H), 3.88 (m, 1H), 3.11 (d, 1H), 3.00 (m, 4H), 2.75 (m, 2H), 2.36 (m, 3H), 1.64 (m, 1H), 1.51 (m, 3H), 1.36 (s, 9H), 1.32 (s, 9H).

Example 4

N$^5$-(tert-Butoxycarbonyl)-N$^2$-[(4-{(2S)-2-[(tert-butoxycarbonyl)amino]-2-carboxyethyl}phenoxy)-carbonyl]-L-ornithyl-S-trityl-L-cysteinamide

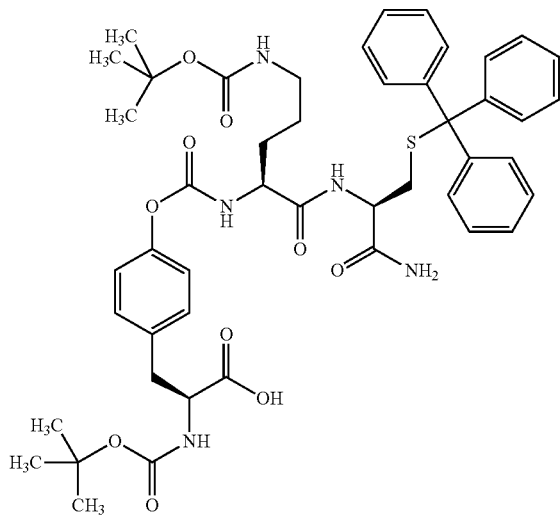 [SMILES: CC(C)(C)OC(=O)NCCC[C@H](NC(=O)Oc1ccc(C[C@H](NC(=O)OC(C)(C)C)C(=O)O)cc1)C(=O)N[C@@H](CSC(c1ccccc1)(c1ccccc1)c1ccccc1)C(N)=O]

5.27 g (5.65 mmol) of the compound from example 12A was dissolved in approx. 60 ml tetrahydrofuran. 2.1 ml (15.2 mmol) Triethylamine, 0.57 ml (15.2 mmol) formic acid and 0.35 g (0.30 mmol) tetrakis(triphenylphosphin)palladium(0) were added. The reaction mixture was stirred over night at room temperature. The reaction was diluted with approx. 60 ml water and twice extracted with approx. 50 ml dichloromethane. The combined organic phases were extracted with brine, dried over sodium sulfate and concentrated to dryness under reduced pressure. The raw product was dissolved in dichloromethane and chromatographed over approx. 500 ml silica gel. Solvents used were dichloromethane, dichloromethane/methanol 20/1 and dichloromethane/methanol 1/1. The product-containing fractions were combined and concentrated to dryness under reduced pressure. The raw product was further purified by preparative RP-HPLC on a C18 column with a water/methanol gradient to yield 1.37 g (24% of theory) product.

LC-MS (method 1): $R_t$=1.17 min., m/z=885 (M+H)$^+$ $^1$H-NMR (400 MHz, DMSO-d$_6$, δ/ppm): δ=12.6 (bs, 1H), 8.05 (d, 1H), 7.97 (d, 1H), 7.06-7.39 (m, 20H), 6.97 (d, 2H), 6.79 (t, 1H), 4.30 (dd, 1H), 4.07 (m, 1H), 4.00 (m, 1H), 2.85-3.04 (m, 3H), 2.30-2.40 (m, 2H), 1.65 (m, 1H), 1.41-1.60 (m, 4H), 1.37 (s, 9H), 1.32 (s, 9H).

Example 5

N-(tert-Butoxycarbonyl)-O-{[(4R,7S)-4-carbamoyl-13,13-dimethyl-6,11-dioxo-1,1,1-triphenyl-12-oxa-2-thia-5,10-diazatetradecan-7-yl]carbamoyl}-L-tyrosine

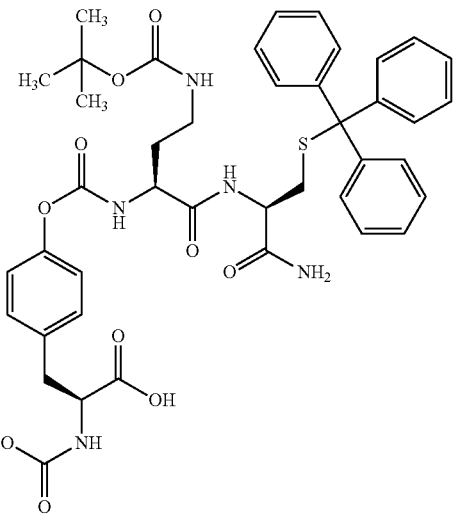

4.91 g (5.40 mmol) of the compound from example 14A was dissolved in approx. 110 ml tetrahydrofuran. 3.8 ml (27 mmol) Triethylamine, 1.02 ml (27 mmol) formic acid and 0.62 g (0.54 mmol) tetrakis(triphenylphosphin)palladium(0) were added. The reaction mixture was stirred over night at room temperature. The reaction was diluted with approx. 60 ml water and twice extracted with approx. 50 ml dichloromethane. The combined organic phases were extracted with brine, dried over sodium sulfate and concentrated to dryness under reduced pressure. The raw product was dissolved in dichloromethane and chromatographed over approx. 500 ml silica gel. Solvents used were dichloromethane, dichloromethane/methanol 40/1 and dichloromethane/methanol 1/1. The product-containing fractions were combined and concentrated to dryness under reduced pressure. The raw product was further purified by preparative RP-HPLC on a C18 column with a water/methanol gradient to yield 1.96 g (42% of theory) product.

LC-MS (method 1): $R_t$=1.20 min., m/z=871 (M+H)$^+$ $^1$H-NMR (400 MHz, DMSO-d$_6$, δ/ppm): δ=12.6 (bs, 1H), 8.05 (t, 2H), 7.16-7.39 (m, 19H), 7.12 (d, 1H), 6.98 (d, 2H), 6.83 (t, 1H), 4.32 (dd, 1H), 4.00-4.11 (m, 2H), 2.92-3.12 (m, 3H), 2.81 (m, 1H), 2.30-2.40 (m, 2H), 1.82 (m, 1H), 1.67 (m, 1H), 1.38 (s, 9H), 1.32 (s, 9H).

Example 6

N-(tert-Butoxycarbonyl)-O-{[(3S)-3-[(tert-butoxy-carbonyl)amino]-4-oxo-4-{[2-(tritylsulfanyl)-ethyl]amino}butyl]carbamoyl}-L-tyrosine

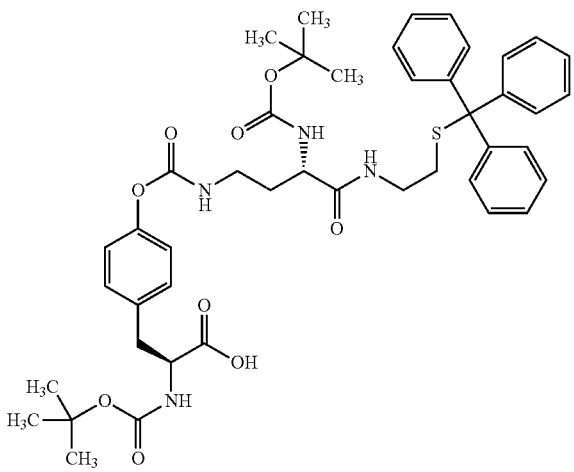 [SMILES: CC(C)(C)OC(=O)N[C@@H](Cc1ccc(OC(=O)NCC[C@H](NC(=O)OC(C)(C)C)C(=O)NCCSC(c2ccccc2)(c2ccccc2)c2ccccc2)cc1)C(=O)O]

98 mg (0.1 mmol) of the compound from example 15A was dissolved in approx. 4 ml tetrahydrofuran. 70 µl (0.5 mmol) Triethylamine, 19 µl (0.5 mmol) formic acid and 11 mg (0.01 mmol) tetrakis(triphenylphosphin)palladium(0) were added. The reaction mixture was stirred over night at room temperature. The reaction was diluted with approx. 5 ml water and twice extracted with approx. 5 ml dichloromethane. The combined organic phases were extracted with brine, dried over sodium sulfate and concentrated to dryness under reduced pressure. The raw product was purified by preparative RP-HPLC on a C18 column with a water/methanol gradient to yield 67 mg (79% of theory) product.

LC-MS (method 1): $R_t$=1.32 min., m/z=827 (M+H)$^+$ $^1$H-NMR (400 MHz, DMSO-d$_6$, δ/ppm): δ=12.6 (bs, 1H), 7.85 (t, 1H), 7.59 (m, 1H), 7.29-7.37 (m, 12H), 7.18-7.27 (m, 5H), 7.07 (bs, 1H), 6.98 (d, 2H), 6.88 (d, 1H), 4.07 (m, 1H), 3.90 (m, 1H), 2.93-3.09 (m, 5H), 2.81 (m, 1H), 2.20 (t, 2H), 1.78 (m, 1H), 1.64 (m, 1H), 1.36 (s, 9H), 1.32 (s, 9H).

Example 7

N-[(2S)-2-[(tert-Butoxycarbonyl)amino]-4-{[(4-{(2S)-2-[(tert-butoxycarbonyl)amino]-2-carboxyethyl}phenoxy)carbonyl]amino}butanoyl]-S-trityl-L-cysteinylglycinamide

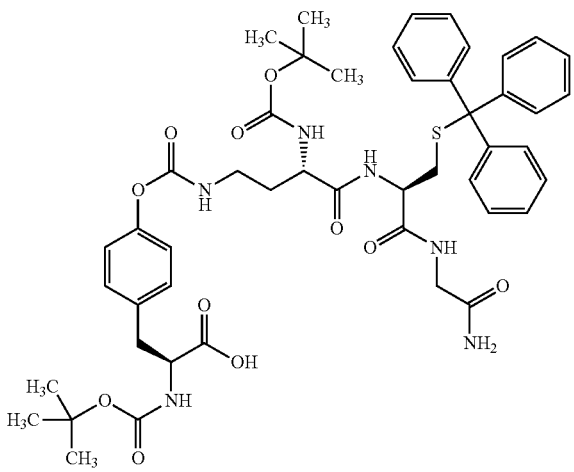 [SMILES: CC(C)(C)OC(=O)N[C@@H](Cc1ccc(OC(=O)NCC[C@H](NC(=O)OC(C)(C)C)C(=O)N[C@@H](CSC(c2ccccc2)(c2ccccc2)c2ccccc2)C(=O)NCC(N)=O)cc1)C(=O)O]

60 mg (0.031 mmol) of the compound from example 16A was dissolved in approx. 3 ml tetrahydrofuran. 22 µl (0.16 mmol) Triethylamine, 6 µl (0.16 mmol) formic acid and 4 mg (0.003 mmol) tetrakis(triphenylphosphin)palladium(0) were added. The reaction mixture was stirred over night at room temperature. The reaction was diluted with approx. 5 ml water and twice extracted with approx. 5 ml dichloromethane. The combined organic phases were extracted with brine, dried over sodium sulfate and concentrated to dryness under reduced pressure. The raw product was purified by preparative RP-HPLC on a C18 column with a water/methanol gradient to yield 26 mg (86% of theory) product.

LC-MS (method 2): $R_t$=2.55 min., m/z=927 (M+H)$^+$ $^1$H-NMR (400 MHz, DMSO-d$_6$, δ/ppm): d=12.6 (bs, 1H), 8.08 (m, 2H), 7.63 (t, 1H), 7.18-7.38 (m, 18H), 7.03-7.15 (m, 3H), 6.99 (d, 2H), 4.28 (dd, 1H), 3.95-4.10 (m, 2H), 3.64 (dd, 1H), 3.51 (m, 1H), 3.04-3.13 (m, 2H), 3.00 (dd, 1H), 2.81 (m, 1H), 2.42 (d, 2H), 1.84 (m, 1H), 1.67 (m, 1H), 1.36 (s, 9H), 1.32 (s, 9H).

Example 8

N-[(2S)-2-[(tert-Butoxycarbonyl)amino]-4-{[(4-{(2S)-2-[(tert-butoxycarbonyl)amino]-2-carboxyethyl}phenoxy)carbonyl]amino}butanoyl]glycyl-S-trityl-L-cysteinamide

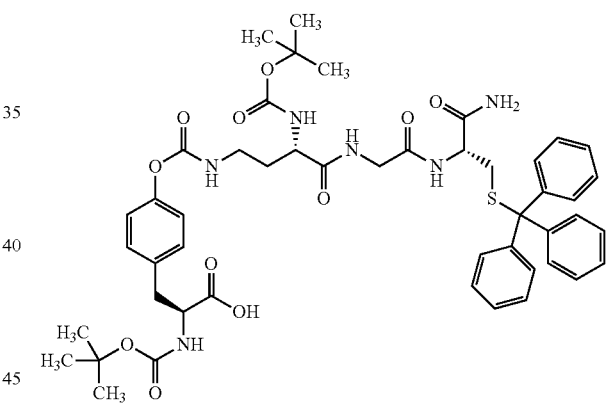

860 mg (0.89 mmol) of the compound from example 19A was dissolved in approx. 20 ml tetrahydrofuran. 620 µl (4.45 mmol) Triethylamine, 168 µl (4.45 mmol) formic acid and 103 mg (0.089 mmol) tetrakis(triphenylphosphin)palladium (0) were added. The reaction mixture was stirred over night at room temperature. The reaction was diluted with approx. 50 ml water and twice extracted with approx. 50 ml dichloromethane. The combined organic phases were extracted with brine, dried over sodium sulfate and concentrated to dryness under reduced pressure. The raw product was purified by preparative RP-HPLC on a C18 column with a water/methanol gradient to yield 329 mg (38% of theory) product.

LC-MS (method 1): $R_t$=1.16 min., m/z=927 (M+H)$^+$ $^1$H-NMR (400 MHz, DMSO-d$_6$, δ/ppm): d=8.16 (d, 1H), 8.04 (t, 1H), 7.64 (t, 1H), 7.20-7.39 (m, 15H), 7.15 (d, 3H), 7.07 (d, 1H), 6.95 (d, 2H), 4.28 (dd, 1H), 4.02 (dd, 1H), 3.91 (m, 1H), 3.76 (m, 2H), 2.99-3.15 (m, 3H), 2.88 (m, 1H), 2.29-2.42 (m, 2H), 1.86 (m, 1H), 1.68 (m, 1H), 1.37 (s, 9H), 1.33 (s, 9H).

Example 9

O-({(3S)-4-[(6-{[(2R)-1-Amino-1-oxo-3-(tritylsulfanyl)propan-2-yl]amino}-6-oxohexyl)amino]-3-[(tert-butoxycarbonyl)amino]-4-oxobutyl}carbamoyl)-N-(tert-butoxycarbonyl)-L-tyrosine

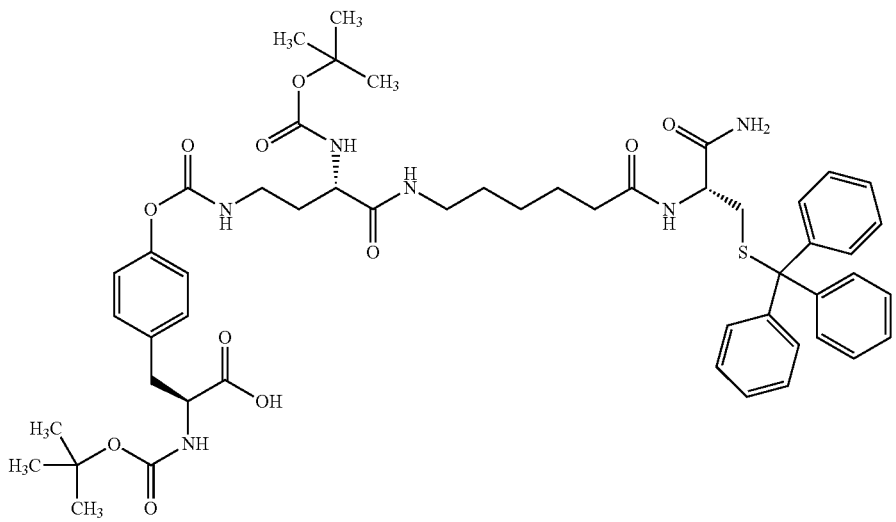 [SMILES: CC(C)(C)OC(=O)N[C@@H](Cc1ccc(OC(=O)NCC[C@H](NC(=O)OC(C)(C)C)C(=O)NCCCCCC(=O)N[C@@H](CSC(c2ccccc2)(c2ccccc2)c2ccccc2)C(N)=O)cc1)C(=O)O]

250 mg (0.24 mmol) of the compound from example 22A was dissolved in approx. 5 ml tetrahydrofuran. 170 µl (1.22 mmol) Triethylamine, 48 µl (1.22 mmol) formic acid and 28 mg (0.024 mmol) tetrakis(triphenylphosphin)palladium(0) were added. The reaction mixture was stirred over night at room temperature. The reaction was diluted with approx. 20 ml water and twice extracted with approx. 20 ml dichloromethane. The combined organic phases were extracted with brine, dried over sodium sulfate and concentrated to dryness under reduced pressure. The raw product was purified by preparative RP-HPLC on a C18 column with a water/methanol gradient to yield 167 mg (65% of theory) product.

LC-MS (method 1): $R_t$=1.19 min., m/z=983 (M+H)$^+$ $^1$H-NMR (400 MHz, DMSO-$d_6$, δ/ppm): d=12.6 (bs, 1H), 8.00 (d, 1H), 7.75 (t, 1H), 7.63 (t, 1H), 7.18-7.37 (m, 19H), 7.12 (d, 1H), 7.08 (s, 1H), 7.00 (d, 2H), 4.31 (m, 1H), 4.06 (m, 1H), 3.93 (m, 1H), 2.92-3.11 (m, 6H), 2.81 (dd, 1H), 2.30 (m, 2H), 2.10 (t, 2H), 1.79 (m, 1H), 1.66 (m, 1H), 1.40-1.54 (m, 3H), 1.37 (s, 9H), 1.32 (s, 9H), 1.23 (in, 2H).

Example 10

O-({(14S)-1-Azido-14-[(tert-butoxycarbonyl)amino]-13-oxo-3,6,9-trioxa-12-azahexadecan-16-yl}carbamoyl)-N-(tert-butoxycarbonyl)-L-tyrosine

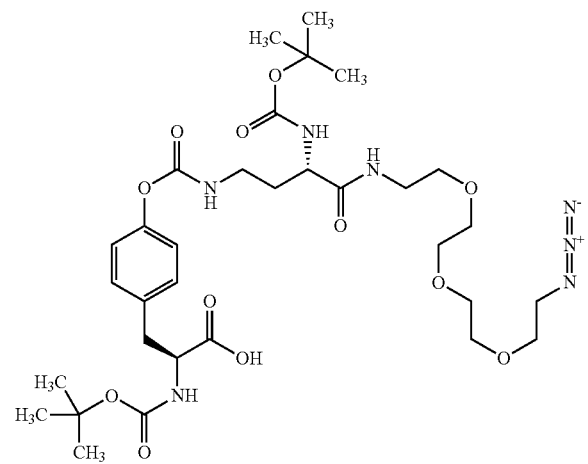 [SMILES: CC(C)(C)OC(=O)N[C@@H](Cc1ccc(OC(=O)NCC[C@H](NC(=O)OC(C)(C)C)C(=O)NCCOCCOCCOCCN=[N+]=[N-])cc1)C(=O)O]

276 mg (0.344 mmol) of the compound from example 23A was dissolved in approx. 15 ml tetrahydrofuran. 235 µl (1.68 mmol) Triethylamine, 63 µl (1.68 mmol) formic acid and 39 mg (0.034 mmol) tetrakis(triphenylphosphin)palladium(0) were added. The reaction mixture was stirred over night at room temperature. The reaction was diluted with approx. 20 ml water and twice extracted with approx. 20 ml dichloromethane. The combined organic phases were extracted with brine, dried over sodium sulfate and concentrated to dryness under reduced pressure. The raw product was purified by preparative RP-HPLC on a C18 column with a water/methanol gradient to yield 167 mg (65% of theory) product.

LC-MS (method 1): $R_t$=0.98 min., m/z=726 (M+H)$^+$ $^1$H-NMR (400 MHz, DMSO-d$_6$, δ/ppm): d=7.85 (t, 1H), 7.61 (t, 1H), 7.15 (d, 2H), 6.91-6.99 (m, 3H), 3.96 (m, 1H), 3.86 (bs, 1H), 3.59 (dd, 2H), 3.46-3.57 (m, 9H), 3.40 (m, 4H), 3.13-3.29 (m, 2H), 2.98-3.11 (m, 3H), 2.82-2.92 (m, 1H), 1.79 (m, 1H), 1.66 (m, 1H), 1.38 (s, 9H), 1.34 (s, 9H).

Example 11

3-[(tert-Butoxycarbonyl)amino]-N-[(4-{(2S)-2-[(tert-butoxycarbonyl)amino]-2-carboxyethyl}-phenoxy)carbonyl]-L-alanyl-S-trityl-L-cysteinamide

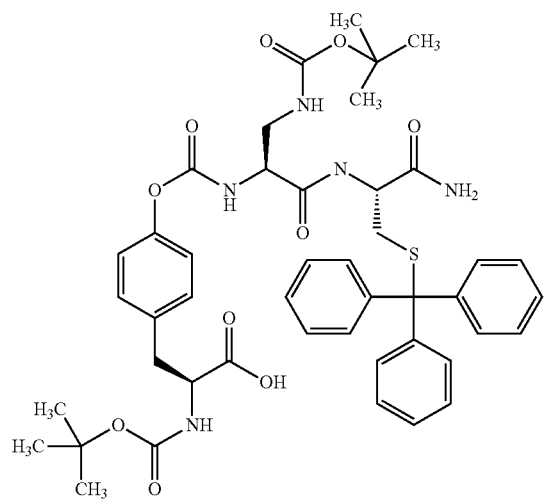 [SMILES: CC(C)(C)OC(=O)NC[C@H](NC(=O)Oc1ccc(C[C@H](NC(=O)OC(C)(C)C)C(=O)O)cc1)C(=O)N[C@@H](CSC(c1ccccc1)(c1ccccc1)c1ccccc1)C(N)=O]

2.38 g (2.03 mmol) of the compound from example 25A was dissolved in approx. 35 ml tetrahydrofuran. 1.42 ml (10 mmol) Triethylamine, 0.38 ml (10 mmol) formic acid and 0.24 g (0.20 mmol) tetrakis(triphenylphosphin)palladium(0) were added. The reaction mixture was stirred over night at room temperature. The reaction was diluted with approx. 20 ml water and twice extracted with approx. 30 ml dichloromethane. The combined organic phases were extracted with brine, dried over sodium sulfate and concentrated to dryness under reduced pressure. The raw product was dissolved in dichloromethane and chromatographed over approx. 70 ml silica gel. Solvents used were dichloromethane/methanol 10/1 to dichloromethane/methanol 1/1. The product-containing fractions were combined and concentrated to dryness under reduced pressure to yield 0.72 g (41% of theory) product.

LC-MS (method 1): $R_t$=1.18 min., m/z=855 (M−H)$^-$ $^1$H-NMR (400 MHz, DMSO-d$_6$, δ/ppm): δ=8.15 (m, 1H), 7.75 (m, 1H), 7.16-7.39 (m, 19H), 6.99 (d, 2H), 6.80 (m, 1H), 4.25 (m, 2H), 4.13 (m, 2H), 4.00 (m, 2H), 2.92-3.12 (m, 3H), 2.81 (m, 1H), 2.40 (m, 2H), 1.38 (s, 9H), 1.32 (s, 9H), 1.10 (m, 4H).

Example 12

O-({(3S)-4-{[(2R)-1-Anilino-1-oxo-3-(tritylsulfanyl)propan-2-yl]amino}-3-[(tert-butoxycarbonyl)-amino]-4-oxobutyl}carbamoyl)-N-(tert-butoxycarbonyl)-L-tyrosine

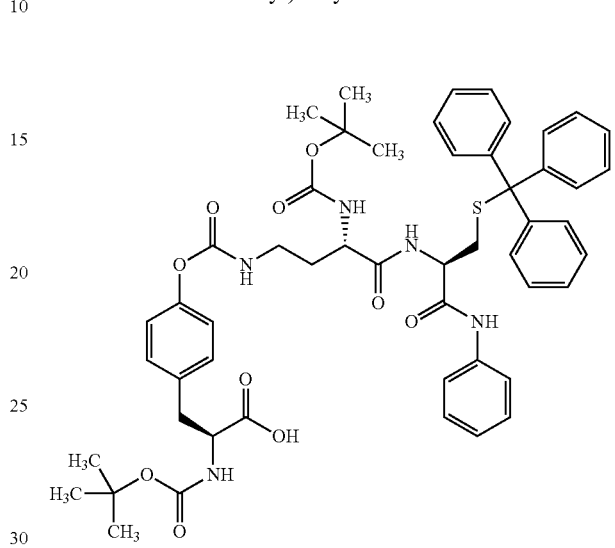

405 mg (0.41 mmol) of the compound from example 26A was dissolved in 10 ml tetrahydrofuran. 0.29 ml (2.05 mmol) triethylamine, 78 µl (2.05 mmol) formic acid and 47 mg (0.04 mmol) tetrakis(triphenylphosphin)palladium(0) were added. The reaction mixture was stirred over night at room temperature. The reaction was diluted with approx. 10 ml water, and twice extracted with approx. 10 ml dichloromethane. The combined organic phases were extracted with brine, dried over sodium sulfate and concentrated to dryness under reduced pressure. The raw product was purified by preparative RP-HPLC on a C18 column with a water/methanol gradient to yield 306 mg (79% of theory) product.

LC-MS (method 1): $R_t$=1.39 min., m/z=947 (M+H)$^+$ $^1$H-NMR (400 MHz, DMSO-d$_6$, δ/ppm): δ=8.08 (d, 1H), 7.60 (m, 1H), 7.55 (m, 1H), 7.28-7.35 (m, 16H), 7.22-7.6 (m, 4H), 7.07 (m, 2H), 6.92 (m, 2H), 4.60 (m, 1H), 4.05 (m, 4H), 2.85-3.20 (m, 4H), 2.80 (m, 1H), 2.45 (m, 2H), 1.85 (m, 1H), 1.66 (m, 1H), 1.35 (d, 18H), 1.28 (m, 2H).

B. ASSESSMENT OF THE CARRIER LINKER ACTIVITY

The suitability of the compounds according to the invention for use as carrier linker can be demonstrated using the following assay systems. To illustrate the different kinetics of different linkers, simple derivatives of the tyrosine based molecule were synthesized and the cleavage at different time points in buffer at pH 4 and pH 7.4 were monitored. Based on the exact composition of the tyrosine based linker structure the formation of the cyclic urea with concomitant release of the free tyrosine OH group has different cleavage kinetics. These can be easily measured in vitro and used as predictors for the in vivo kinetics. Scheme 3 shows exemplaric the decomposition of a prodrug releasing the tyrosine containing peptide and a cyclic urea derivative based on the former linker with the modifier attached.

Scheme 3

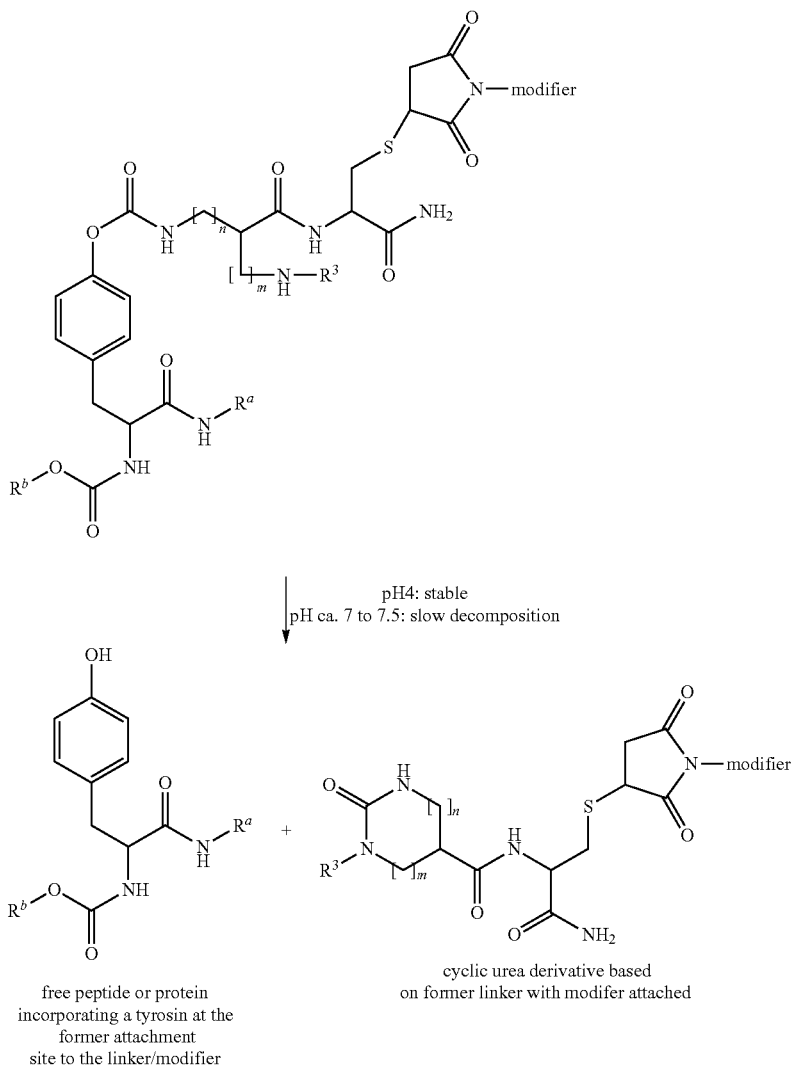

free peptide or protein incorporating a tyrosin at the former attachment site to the linker/modifier cyclic urea derivative based on former linker with modifer attached With example 1C, O-{[(3S)-3-Amino-4-({(2R)-1-amino-3-[(1-benzyl-2,5-dioxopyrrolidin-3-yl)sulfanyl]-1-oxopropan-2-yl}amino)-4-oxobutyl]carbamoyl}-N-phenyl-L-tyrosinamide, the cleavage reaction is as follows:

Scheme 4

-continued

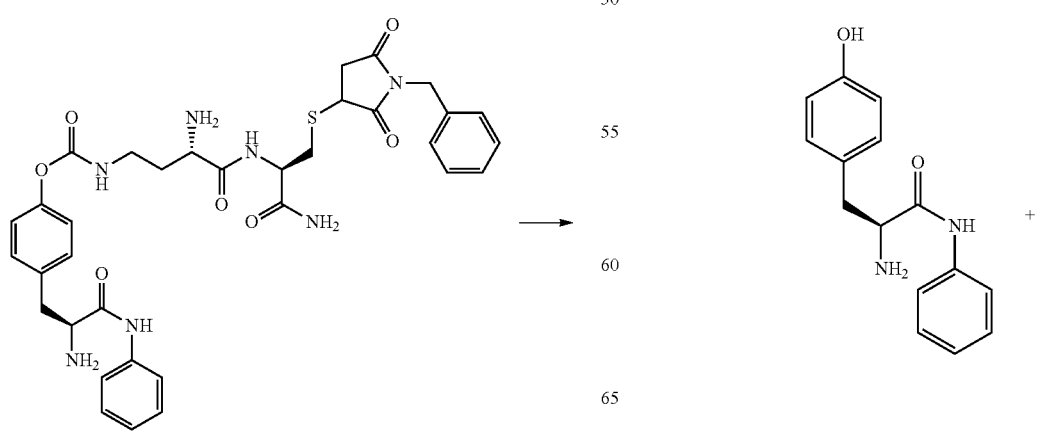

-continued

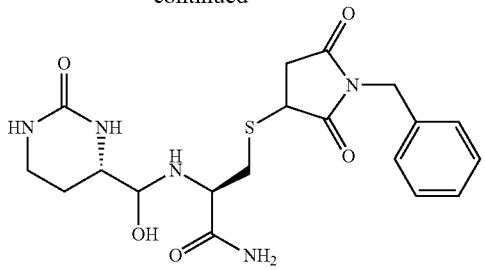

1) Test Description (In Vitro)

For the kinetic studies with regard to the stability of the different linkers 0.3 mg of the dry test compound are dissolved in 0.5 ml acetonitrile. For a better dilution the sample is sonified for about 10 seconds. Then 1.0 ml of the buffer solutions are added and the samples are sonified again.

Chemical composition of the solution/buffer which are used:
pH 4: 1 liter of deionized water was adjusted to pH 4 with 1N hydrochloric acid
pH 7.4: 90 g sodium chloride, 13.61 g potassium dihydrogene phosphate and 83.35 g 1 M sodium hydroxide solution were dissolved in 1 liter of deionized water. This solution was diluted with water at the rate of 1:10.

The test compound concentration is analysed by HPLC every hour during 24 hours at room temperature. The quantity of the test compound is determined by the peak areas.

HPLC method: Agilent 1100 with DAD (G1315B), binary pump (g1312A), autosampler (G1329A), column thermostat (G1330B), Column: Kromasil 100 C18/250 mm×4 mm/5 μm, Column temperature: 30° C., Eluent A: water+5 ml perchloric acid/1, Eluent B: acetonitrile, Gradient: 0-1.0 min 90% A, 10% B; 1.0-20.0 min 10% A, 90% B; 20.0-21.0 min 10% A, 90% B; 21.0-23.0 min 90% A, 10% B; 23.0-25.0 min 90% A, 10% B; Flow rate: 1.5 ml/min, Detection: 210 nm, Injection volume: 10 μl.

The results of the cleavage of the test compounds are shown in Table 1.

TABLE 1

| Example No | % cleaved pH 4, 0 h | % cleaved pH 4, 24 h | % cleaved pH 7.4, 0 h | % cleaved pH 7.4, 6 h | % cleaved pH 7.4, 24 h |
|---|---|---|---|---|---|
| 1C | 0 | 1 | 0 | 7 | 21 |
| 2C | 0 | 0 | 0 | 6 | 21 |
| 3C | 0 | 0 | 0 | 2 | 11 |
| 4C | 0 | 0 | 0 | 23 | 65 |
| 5C | 0 | 0 | 0 | 75 | 100 |
| 6C | 0 | 0 | 0 | 6 | 20 |
| 7C | 0 | 0 | 0 | 6 | 23 |
| 8C | 0 | 0 | 0 | 6 | 23 |
| 9C | 0 | 0 | 0 | 7 | 25 |
| 10Cb | 0 | 0 | 0 | 4 | 14 |
| 11C | 0 | 19 | 0 | 100 | 100 |
| 12C | 0 | 0 | 0 | 29 | 76 |

The data show that example 11C is cleaved very quickly, even at pH4. Example 4C, example 5C and example 12C are cleaved quickly whereas example 3C and example 10Cb are cleaved slowly. All others have a moderate cleavage kinetic.

C. EXEMPLARY EMBODIMENTS OF PHARMACEUTICAL COMPOSITIONS

The compounds according to the invention can be converted into pharmaceutical preparations in the following ways:

i.v. Solution:
A compound according to the invention is dissolved at a concentration below saturation solubility in a physiologically acceptable solvent (for example buffers of pH 4 to pH 7, isotonic sodium chloride solution, glucose solution 5% and/or PEG 400 solution 30%). The solution is sterilized by filtration and filled into sterile and pyrogen-free injection containers.

s.c. Solution:
A compound according to the invention is dissolved at a concentration below saturation solubility in a physiologically acceptable solvent (for example for example buffers of pH 4 to pH 7, isotonic sodium chloride solution, glucose solution 5% and/or PEG 400 solution 30%). The solution is sterilized by filtration and filled into sterile and pyrogen-free injection containers.

The invention claimed is:
1. A compound of the formula

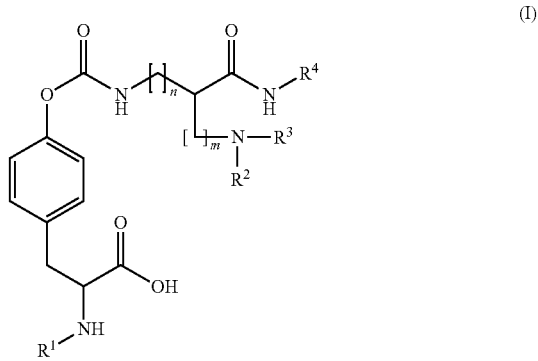

(I)

wherein
n represents the number 0, 1, 2, 3 or 4,
m represents the number 0, 1, 2, 3 or 4,
where m and n together are the number 1, 2, 3, 4, 5 or 6,
$R^1$ represents tert-butyloxycarbonyl or (9H-fluoren-9-yl-methoxy)carbonyl,
$R^2$ represents tert-butyloxycarbonyl,
$R^3$ represents hydrogen, methyl, ethyl, n-propyl, isopropyl or benzyl,
$R^4$ represents a group of the formula

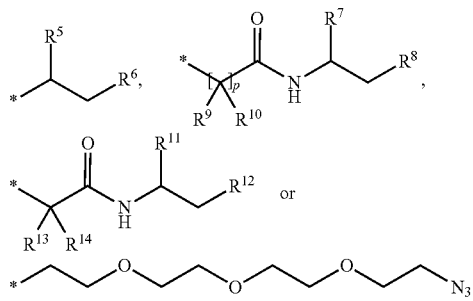

where
* is the point of attachment to the nitrogen,
p represents the number 1, 2, 3, 4 or 5,
$R^5$ represents hydrogen, aminocarbonyl, $(C_1$-$C_4)$-alkylaminocarbonyl, phenylaminocarbonyl or a group of the formula

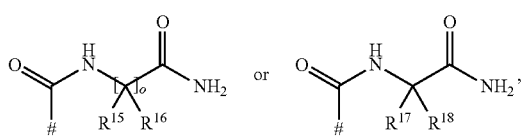

where
# is the point of attachment to the carbon atom,
o represents the number 1, 2, 3, 4 or 5,
$R^{15}$ represents hydrogen or $(C_1\text{-}C_4)$-alkyl,
$R^{16}$ represents hydrogen or $(C_1\text{-}C_4)$-alkyl,
$R^{17}$ represents the side group of a natural α-amino acid or its homologues or isomers,
and
$R^{18}$ represents hydrogen or methyl,
$R^6$ represents —S-trityl, thiolyl, azidyl, acetylenyl, hydroxycarbonyl or amine,
$R^7$ represents hydrogen or aminocarbonyl,
$R^8$ represents —S-trityl, thiolyl, azidyl, acetylenyl, hydroxycarbonyl or amine,
$R^9$ represents hydrogen or $(C_1\text{-}C_4)$-alkyl,
$R^{10}$ represents hydrogen or $(C_1\text{-}C_4)$-alkyl,
$R^{11}$ represents hydrogen or aminocarbonyl,
$R^{12}$ represents —S-trityl, thiolyl, azidyl, acetylenyl, hydroxycarbonyl or amine,
$R^{13}$ represents the side group of a natural α-amino acid or its homologues or isomers,
and
$R^{14}$ represents hydrogen or methyl,
or a salt thereof.

2. The compound of claim 1, wherein
n represents the number 0, 1, 2 or 3,
m represents the number 0, 1, 2 or 3,
where m and n together are the number 1, 2, 3 or 4,
$R^1$ represents tert-butyloxycarbonyl or (9H-fluoren-9-yl-methoxy)carbonyl,
$R^2$ represents tert-butyloxycarbonyl,
$R^3$ represents hydrogen, methyl, ethyl, n-propyl, isopropyl or benzyl,
$R^4$ represents a group of the formula

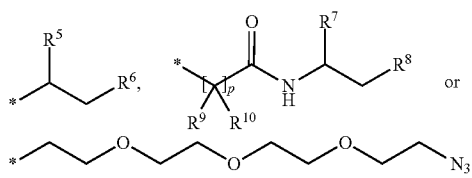

where
* is the point of attachment to the nitrogen,
p represents the number 1, 2, 3, 4 or 5,
$R^5$ represents hydrogen, aminocarbonyl, phenylaminocarbonyl or —(C=O)NHCH$_2$(C=O)NH$_2$,
$R^6$ represents —S-trityl,
$R^7$ represents hydrogen or aminocarbonyl,
$R^8$ represents —S-trityl,
$R^9$ represents hydrogen,
and
$R^{10}$ represents hydrogen.

3. The compound of claim 1, wherein
n represents the number 2 or 3,
and
m represents the number 0,
or
n represents the number 0,
and
m represents the number 2 or 3,
or
n represents the number 0,
and
m represents the number 1,
$R^1$ represents tert-butyloxycarbonyl or (9H-fluoren-9-yl-methoxy)carbonyl,
$R^2$ represents tert-butyloxycarbonyl,
$R^3$ represents hydrogen, methyl, ethyl, n-propyl, isopropyl or benzyl,
$R^4$ represents a group of the formula

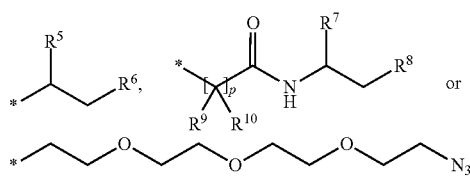

where
* is the point of attachment to the nitrogen,
p represents the number 1, 2, 3, 4 or 5,
$R^5$ represents hydrogen, aminocarbonyl, phenylaminocarbonyl or —(C=O)NHCH$_2$(C=O)NH$_2$,
$R^6$ represents —S-trityl,
$R^7$ represents hydrogen or aminocarbonyl,
$R^8$ represents —S-trityl,
$R^9$ represents hydrogen,
and
$R^{10}$ represents hydrogen.

4. A process for preparing a compound of the formula (I) or a salt thereof, comprising
reacting a compound of the formula (II)

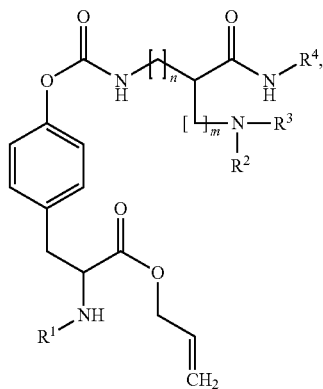

(II)

in which
n, m, $R^1$, $R^2$, $R^3$ and $R^4$ are each as defined in claim 1,
with a Palladium(0) source and a reducing agent.

5. A pharmaceutical composition comprising a prodrug prepared with a compound of claim 1 and an inert nontoxic pharmaceutically suitable excipient.

6. The pharmaceutical composition of claim 5, further comprising a further active ingredient.

* * * * *